US012588834B2

(12) United States Patent
Kaltenbach et al.

(10) Patent No.: US 12,588,834 B2
(45) Date of Patent: Mar. 31, 2026

(54) DEVICE, SYSTEM AND METHOD FOR MOVEMENT TRACKING

(71) Applicant: Forstgarten International Holding GmbH, St. Gallen (CH)

(72) Inventors: Stefan Kaltenbach, St. Gallen (CH); Johannes Landgraf, St. Gallen (CH)

(73) Assignee: Forstgarten International Holding GmbH, St. Gallen (CH)

( * ) Notice: Subject to any disclaimer, the term of this patent is extended or adjusted under 35 U.S.C. 154(b) by 786 days.

(21) Appl. No.: 17/436,784

(22) PCT Filed: Mar. 12, 2020

(86) PCT No.: PCT/EP2020/056716
§ 371 (c)(1),
(2) Date: Sep. 7, 2021

(87) PCT Pub. No.: WO2020/182962
PCT Pub. Date: Sep. 17, 2020

(65) Prior Publication Data
US 2022/0167876 A1 Jun. 2, 2022

(30) Foreign Application Priority Data
Mar. 12, 2019 (DE) .................... 10 2019 106 310.8

(51) Int. Cl.
*A61B 5/11* (2006.01)
*A61B 5/00* (2006.01)
(52) U.S. Cl.
CPC .......... *A61B 5/1114* (2013.01); *A61B 5/1121* (2013.01); *A61B 5/682* (2013.01);
(Continued)

(58) Field of Classification Search
CPC ..... A61B 5/1114; A61B 5/1121; A61B 5/682; A61B 2560/0223; A61B 2562/0219; A61B 5/4542; A61B 5/1111
See application file for complete search history.

(56) References Cited

U.S. PATENT DOCUMENTS

2011/0053110 A1* 3/2011 Bando .................. A61B 5/1126
433/68
2016/0051879 A1* 2/2016 Reynolds, III ....... A61B 5/1121
700/91
(Continued)

FOREIGN PATENT DOCUMENTS

JP        4665051 B2    1/2011
WO     2016044251 A1    3/2016

OTHER PUBLICATIONS

"IEEE Recommended Practice for Inertial Sensor Test Equipment, Instrumentation, Data Acquisition, and Analysis", IEEE Standard (2005).
(Continued)

*Primary Examiner* — Jason M Sims
*Assistant Examiner* — Kyle W. Kretzer
(74) *Attorney, Agent, or Firm* — McDonnell Boehnen Hulbert & Berghoff LLP

(57) ABSTRACT

The invention relates to a system for detecting the relative movement of body parts, the system having at least two subsystems, i.e. a first subsystem and a second subsystem, wherein the first subsystem is designed to be fastened to a first body part, for example the upper jaw, or a body region rigidly connected to the upper jaw, such as the skull, and the second subsystem is designed to be fastened to a second body part, for example the lower jaw, wherein the first body part and the second body part are movable relative to each other, and wherein the system comprises a movement sensor system and a calibration sensor system, wherein
(Continued)

Figure 1:
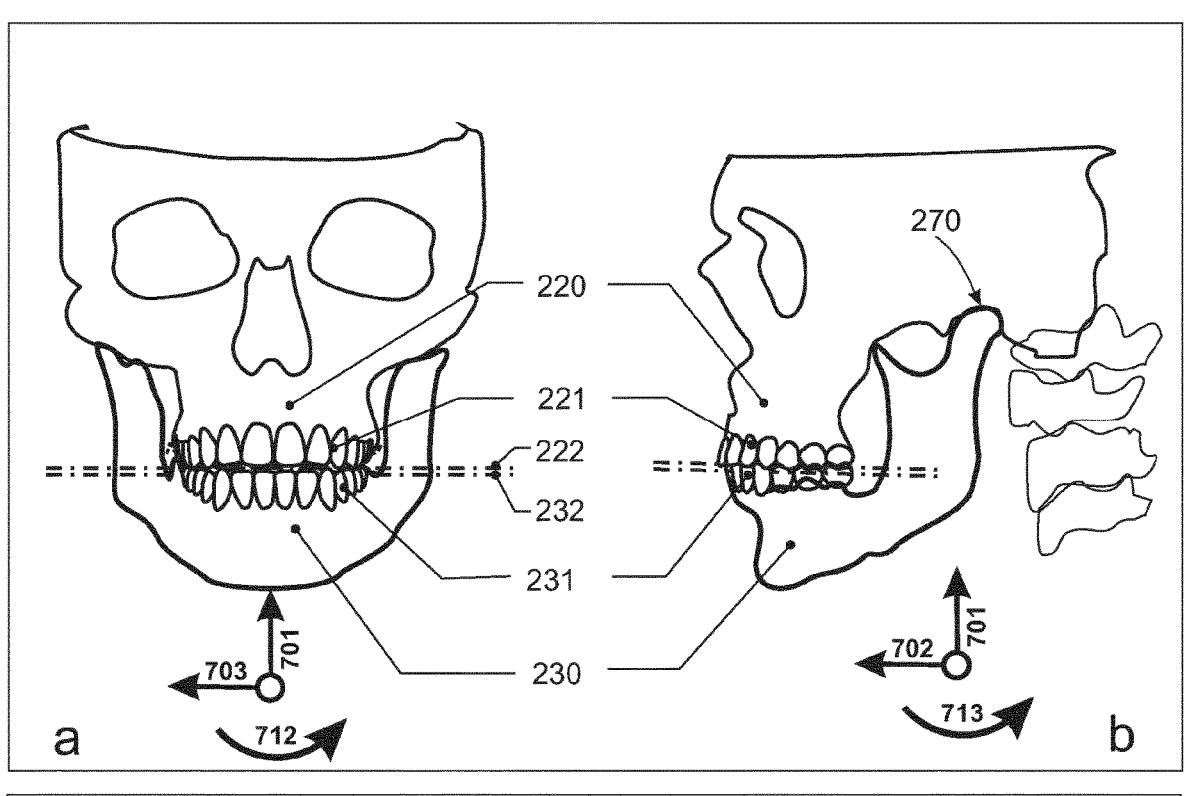
Figure 1:
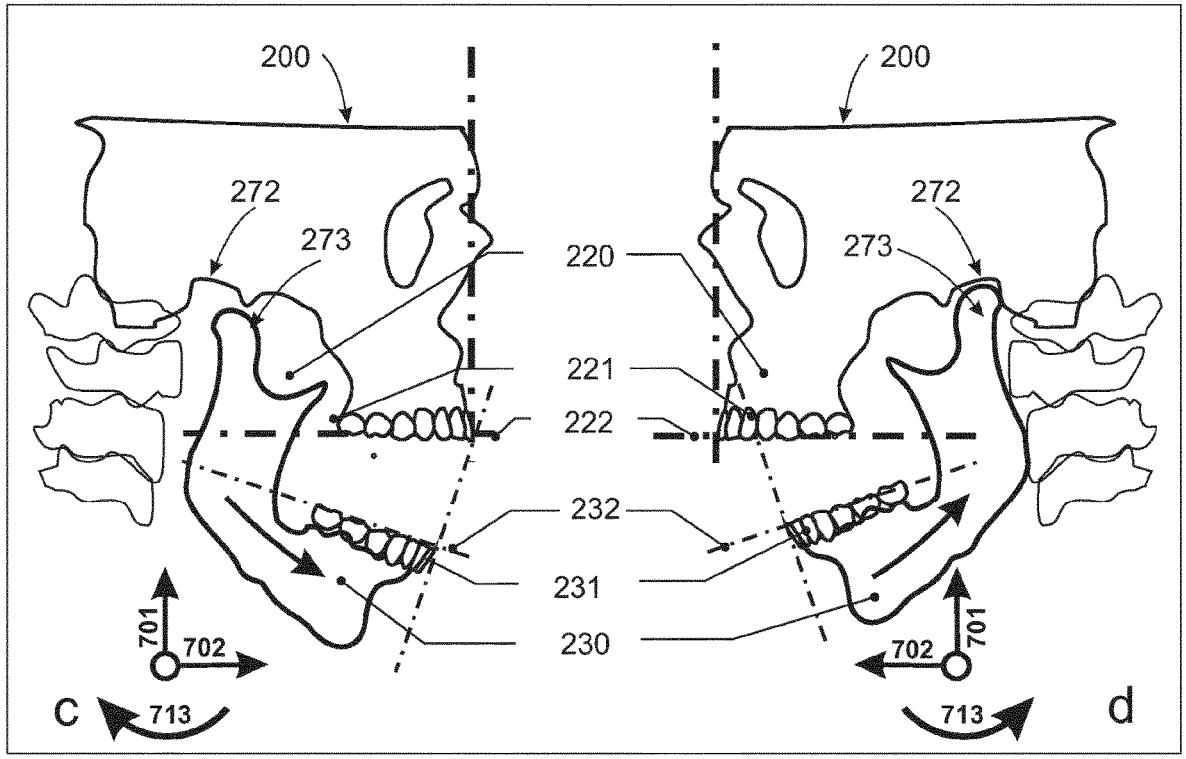

the movement sensor system is designed to detect the relative movement or relative positions of the first body part and the second body part across a movement range, for example by generating data from which the movement trajectory or course of the relative movement of the first body part and of the second body part can be obtained or is obtained, and the calibration sensor system is designed to determine the relative position of the first body part relative to the second body part if (for example only if and/or always if) the first body part and the second body part are arranged relative to each other, preferably close to each other, in a calibration region.

50 Claims, 12 Drawing Sheets

(52) U.S. Cl.
CPC ................. *A61B 2560/0223* (2013.01); *A61B 2562/0219* (2013.01)

(56) References Cited

U.S. PATENT DOCUMENTS

| | | | | |
|---|---|---|---|---|
| 2016/0128624 A1* | 5/2016 | Matt | .................... | A61C 19/045 |
| | | | | 600/301 |
| 2016/0331316 A1* | 11/2016 | Allen | ................. | A63B 24/0021 |
| 2018/0055420 A1* | 3/2018 | Gassler | ................ | A61B 5/4542 |

OTHER PUBLICATIONS

International Search Report for corresponding PCT application No. PCT/EP2020/056716 dated May 14, 2020.

* cited by examiner

DEVICE, SYSTEM AND METHOD FOR MOVEMENT TRACKING

FIELD OF THE INVENTION

The invention relates to the metrological detection of complex jaw positions and of movements of the jaw and the head by an intraoral device or by devices mounted on the dentition, for a short time or for a longer period, in particular for movement analyses lasting several hours, during exercise, stress and sleep.

BACKGROUND

The following observations are to be understood as background to the disclosed invention and not as an admission that any of the features discussed constitute prior art. Furthermore, features disclosed in this section can also be combined with further features from other sections of the present disclosure.

The dimensions or degrees of freedom of movement generally comprise three mutually orthogonal translation directions and three mutually perpendicular rotation axes. In this context, the physical term 6-degrees-of-freedom is used to define three translational position coordinates and three rotational spatial orientation coordinates. Movements of real bodies are characterized by the change in the 6-degrees-of-freedom coordinates.

Movement can be measured by coupling measuring devices to moving objects. If the movement of the upper jaw is measured, this entails the movement of the head, provided it is not deformed and vice versa. If the movement of the lower dental arch is measured or even just an implant in the lower jaw, the movement of the lower jaw is detected as long as the detected sub-object (for example an implant) moves along with the larger object (for example the lower jaw) without relative movement. The fixed coupling is therefore a key requirement for a high degree of measurement accuracy. The position and orientation of the body part result from the position and orientation of the device detected in its movement by 6-degrees-of-freedom coordinate transformation.

Particularly in biomechanics, relative positions and relative movements between body parts are to be recorded. This is described below using the example of the jaw and the dental arches. Here, for example, both the position or movement of the upper jaw OK and the position or movement of the lower jaw UK are detected. The relative movement of the lower jaw UK relative to the upper jaw OK results from coordinate transformation into the moving reference system of the upper jaw. The reference system of the upper jaw OK with its three orthogonal spatial axes is shown schematically in FIG. 1 and in FIG. 3 to FIG. 11. Viewed in the sagittal plane of the dentition, the reference system has two spatial directions, namely 701 upward and 702 forward. The opening movement of the lower jaw predominantly follows the rotation direction 713, which strictly speaking entails a complex six-dimensional movement that is superimposed from, for example, several translations and rotations. A person skilled in the art is familiar with representing six-dimensional movements as six-dimensional matrices and with describing relative movements likewise six-dimensionally in matrix form.

Many different devices and methods have been proposed in connection with the movements of the masticatory apparatus, the temporomandibular joint and/or the teeth with respect to one another.

For example, it is worth mentioning the devices from the company Zebris, which transmit the movement of the lower jaw via a coupling element to a lower-jaw fork, the movement of this lower-jaw fork being detected by a measuring system attached to the head above the nose. The relative movement is thus detected directly by the for example optical upper sensors in their position relative to the markers on the lower-jaw fork.

Also of importance in the market are the systems from the companies DDI and Orangedental for measuring movement with digital cameras, wherein both the movement of the lower jaw and that of the upper jaw or of the head are measured by a camera system that is mounted in a fixed spatial position. The head movement is also measured here, separately from the movement of the lower jaw; the relative movement results from the coordinate transformation of the positions of the lower jaw into the optionally moving coordinate system of the upper jaw or head.

A mixed form is offered by the company Planmeca. A pair of spectacles carries several marker spheres, and a small measuring bow guided outward from the lower jaw also carries several marker spheres, each as marker systems, which move relative to one another with the chewing movement and the opening of the mouth. The detection is carried out with several cameras at an angle from the front. As a special feature, the cameras are integrated in a DVT head X-ray device. The marker systems are so closely adjacent that they do not obstruct the circular movement of the DVT camera arc.

In addition, measurement methods are commercially available with which tracking is possible, in particular for protrusion splints that are prescribed against snoring and sleep apnea. A gravity sensor is integrated in one part of the splint and detects the spatial position of the splint and whether there are random natural head and jaw movements. However, these devices are not very suitable for detecting the relative movement and position data between upper jaw and lower jaw, because the problem of the cumulative sum of the measurement errors is currently not resolved in the case of translational and rotational movements that repeatedly return to the starting point.

For other parts of the body that are detected in movement, for example the legs, stockings with markings can be applied so that these markings can be tracked during sport. This does not work with the oral mucosa, and it is impossible to track marked teeth with cameras from the outside when the mouth is closed. If one were to mark the incisors and lift the lips, a very unnatural behavior would arise after a short time, i.e. very different from the case of an athlete with the marker stockings on his or her legs.

The precise measuring methods which are described, some of which are patent pending and some of which are also on the market, all work with frames, forks or brackets extending outward as part of the marker system. These outwardly extending devices are fundamentally unsuitable for use when sleeping or at work, in particular for detecting movement in stressful situations, etc., because they would be deformed or even destroyed and would also impede the natural movement of the body or change the movement sequences.

Alternative measurement methods, e.g. Ignident, use a magnetic field generator that is placed above the head and generates a usable and/or known magnetic field in the oral cavity. As a result, magnetic field sensors located in the mouth, usually a sensor for the lower jaw and/or a sensor for the upper jaw, can detect the local magnetic field strengths and determine therefrom the 6 degrees of freedom coordinates relative to the magnetic field generator. This means in practice that, for the entire duration of the measurement, the patient or test person has to be present in the spatially very narrowly limited, evaluable magnetic field region below the magnetic field generator, which is also not practicable over a longer period of time.

Finally, the patent application from Forstgarten (WO 2016/142264 A1) discloses an internal marking or a sensor which is attached to the lower jaw and which could be detected e.g. with a camera from the upper jaw. However, the volume taken up poses a problem and the tongue obstructs the view. In addition, the question of the energy supply for an autonomous intraoral sensor, without an external power feed, has not been resolved.

The main problem with integral sensors that could be used for such applications is that they either have too coarse a resolution and too large a measuring range, such that they cannot correctly detect the fine contact movements and contact positions, such as those of the upper jaw and/or lower jaw, with small velocities, small accelerations and/or small amplitudes. Or they have such a small resolution and/or such a small measuring range that they cannot correctly detect the sweeping relative movements, such as those of the upper jaw and/or lower jaw at high speeds, great accelerations and/or great amplitude, for example when yawning. In practice, however, both measuring ranges are needed with complete or great accuracy. Integral sensors are sensors in which the generated signal is characteristic of a parameter (e.g. acceleration), wherein at least one integration, in particular over time, is required to determine the or a measured quantity to be determined (e.g. position and/or speed) or several integration processes may have to be carried out.

In the case of integral sensors, particular problems can arise because, in the integration with available sensors that measure the acceleration and/or the speeds or rotation rates, either the particularly slow movements in the integral are not correctly detected and/or the particularly rapid movements are also not correctly recorded. As a result, the integral of the detected movement in a complex movement such as that of the lower jaw relative to the upper jaw is not exactly correct. As a consequence, the integral of a repetitively recurring movement such as the chewing movement or the movement of the head and jaw while sleeping is incorrect and leads to continually increasing miscalculations with regard to the position of the upper jaw and lower jaw or their relative position.

There has thus far been no possible way of carrying out a really precise measurement of the jaw movement—lower jaw and upper jaw relative to each other—and at the same time the head movement in space, for example in the sense of long-term 6-degrees-of-freedom detection, in a natural undisturbed situation, e.g. while sleeping, preferably without significantly altering or impeding the natural movements.

Object of the Invention

A fundamental object of the invention is to provide improvements in the field of movement tracking of body parts.

A further or alternative object to be achieved is to make available a practical device, a system and a method that permit or facilitate the detection of positions and movements of the lower jaw and the head and/or the upper jaw within short measurement periods, for example a few seconds or minutes, but also within longer measuring periods of several hours under the most natural conditions possible. The system should be integrated or be able to be integrated in the mouth for the most natural circumstances possible. The measurement should be possible without complex receivers or transmitters having to be fitted around the head. However, the invention is not necessarily limited to this. Since mainly rigid fastening devices are able to transfer the movement in their six-dimensional coordinates to other positions, the movement sensors that can be used within the scope of the invention can also be attached to fastening devices, which are then in turn attached to the body parts or are provided for corresponding attachment. For example, the fastening devices can be attached to the upper jaw or the lower jaw. In addition, for long-term use, no sensitive and troublesome measuring bows should be guided out from the mouth or placed on the outside.

A further or alternative object to be achieved is to finally facilitate or permit an exact detection of the fine contact movements of the teeth, for example when chewing, and/or to facilitate or permit an exact detection of the sweeping movement of the jaws, for example when yawning or shouting, preferably with the same system and/or the same sensors, preferably integrating sensors. This is not a routine matter, since the integrating sensors available to date do not succeed in doing both at the same time, i.e. measuring fine movement and sweeping movement. The problem is particularly evident from the fact that either the rapid and/or the slow movements or the movements with extreme values of speed and/or acceleration are not correctly detected and, consequently, the metrologically detected trajectory of the combined translational and rotational movement does not exactly correspond to the real movement. As a direct consequence, a movement in the measurement that actually leads to a definable point leads to an apparent end point that differs by a measurable translation and/or rotation difference. Such errors add up in the course of long-term movement tracking. One object to be achieved now is to offer a system and a method with the aid of which the problem of cumulative measurement errors can be solved.

One goal may be in particular to be able to carry out the 6-degrees-of-freedom movement detection in the temporomandibular joint and on the head during sports, during stressful work and/or when lying in bed, e.g. while sleeping. Particularly preferred is a solution with the aid of which the jaw movements and head movements of a patient can be followed day and night at home or in hospital, without troublesome equipment being attached to the head. It is advantageous here, especially as a secondary goal, that the activity of the sensor system is also ensured in terms of energy consumption to such an extent that the measurement can be carried out over at least one or a few hours, without external energy having to be supplied via cables that impede movement.

Proposed Solution(s)

At least one of the abovementioned objects is achieved by the subject matter of the independent claim/independent claims. Advantageous developments of the subject matter of the independent claims are characterized in the subclaims. The wording of all the claims is hereby incorporated by reference into the content of this description. The use of the singular is not intended to exclude the plural, which also applies in the opposite sense, unless otherwise indicated. In addition, it will be noted that the disclosure is not restricted by the claims and instead can contain other advantageous concepts and solutions that are not currently claimed.

Individual devices and method steps and the system are described in more detail below. In the description of the device, the reference to the body parts that move relative to each other, for example upper jaw OK and lower jaw UK, can be interchangeable. This is because if the lower jaw moves relative to the upper jaw, this is equivalent to a relative movement of the upper jaw to the lower jaw. All body parts in turn can move with six degrees of freedom in real space. Moreover, instead of the movement of the dental arches, either the movement of the upper jaw can be detected or the movement of the cranial bone, since the latter is normally firmly connected by bone to the upper jaw.

Fields of application of the proposed solution are in particular diagnostics, analysis, training and therapy in connection with temporomandibular joint functions and dentition functions, in particular with the static and dynamic position and movement of the lower jaw relative to the upper jaw and the associated temporomandibular joint conditions. These measurements have particular application for the digital planning and production of dentures, orthodontic devices and for use in sleep medicine, e.g. in sleep apnea, which is characterized by the lower jaw and tongue falling back in a relaxed state while sleeping, thereby closing the airways.

A special feature that can be achieved with the claimed solution is that the mode of action of at least two different sensors or two sensor technologies can be combined in one system in such a way that the otherwise cumulative measurement errors of the movement detection can be corrected during the movement or after movement segments. In particular, the system can be designed for a trajectory correction and/or a correction of the measured values for speed and/or acceleration both for translation and for rotation and preferably combined movements in up to six degrees of freedom. The proposed system for measuring and/or tracking movement comprises at least one first sensor system S_motion (movement sensor system), for example for detecting acceleration and/or speed. Alternatively or in addition, the path can also be detected directly or indirectly, with this being able to detect the entire trajectory or a quite large region of the trajectory of a body part in space or relative to another body part. The proposed system preferably also comprises at least one second sensor system (e.g. S_calibration or calibration sensor system). This second sensor system detects a subregion, preferably only a subregion, of the movement region detected by S_motion. In the subregion, the second sensor system preferably has a region of high measurement accuracy in detecting at least the position and/or spatial orientation of the body. The region of high measurement accuracy can be intrinsically predefined by the design of the sensor system or can be specified by the manufacturer. The accuracy of the second sensor system is preferably greater than the accuracy that can be achieved with the first sensor system. S_calibration preferably works with at least twice the accuracy of the first sensor system S_calibration, particularly preferably with at least four times the accuracy. The body parts movable relative to one another preferably carry parts of the first sensor system S_motion and also parts of the second sensor system S_calibration. As soon as the moving body is located in the region of high measurement accuracy of the second sensor system S_calibration, at least one measurement result from S_calibration is used to initiate or carry out a recalibration or a correction of the measurement values of the sensor system S_motion. The correction carried out ensures that the measurement values or the values determined on the basis of the measurement values of the first sensor system S_motion for e.g. acceleration, speed and/or translational and rotational trajectories are adapted to the more precise measurement values of the sensor system S_calibration. This completely or partially corrects any deviation of the movement coordinates determined by S_motion from the real movement. The system is preferably designed such that the sensor parameters can also be recalibrated using the information from the sensor system S_calibration. Particularly preferably, a processor unit or device and a storage device are used to correct the measurement values obtained from the first sensor system S_motion, in particular also retrospectively in time, for example in the sense that, at least in the zero derivation of the location, the trajectory is matched to the at least one position determined by the second sensor system S_calibration. The speed and/or acceleration are also preferably matched. This compensates for abrupt effects of the correction, and a translational and rotational trajectory is determined that corresponds as closely as possible to reality. If this matching correction were not carried out, there would be a danger that the sequence of the six-dimensional trajectory corrected by means of S_calibration would appear erratic. This could be misinterpreted as a physique-related or disease-related movement disorder with abrupt acceleration. The proposed correction achieves a high level of accuracy in the position. In the extended match, the most realistic possible detection of the speed and acceleration can be simplified.

As a result of this correction/calibration, which is preferably repeated during the measuring time or operating time, expediently often enough for a desired accuracy, the movement or the relative movement can be detected with a high degree of accuracy over a long period of time, e.g. 8 hours or more. In the dental sector, it is typically required to detect movement precisely to within ten to one hundred micrometers, generally precisely to between one and a thousand micrometers. Such a high degree of precision is advantageous or even necessary, because changes in position of ten to one hundred micrometers are decisive for the formation of contact on the teeth. Measurement times of up to twelve hours are also typical for movement detection during sleep, which ultimately means that the required accuracy should still be available even after twelve hours. While this is absolutely impossible with previously available integral sensors, the proposed solution is able to meet these requirements. The proposed solution preferably includes a device or a system for supplying energy to the at least partially active sensor system. In the preferred embodiment, the detection data are either temporarily stored, for example in a data memory in the device, and are transmitted to an evaluation system after the measurement phase, or the transmission is preferably wireless during the measurement, preferably using one of the available radio standards.

Advantageous developments and refinements are the subject matter of the dependent claims and/or result from the following description in conjunction with the figures.

LIST OF THE FIGURES

FIG. 1 shows the skull 200 with upper jaw 220 and lower jaw 230 and dental arches 221, 231 and, schematically indicated, the basically always six-dimensional coordinate system for translations and rotations.

Figure 2:
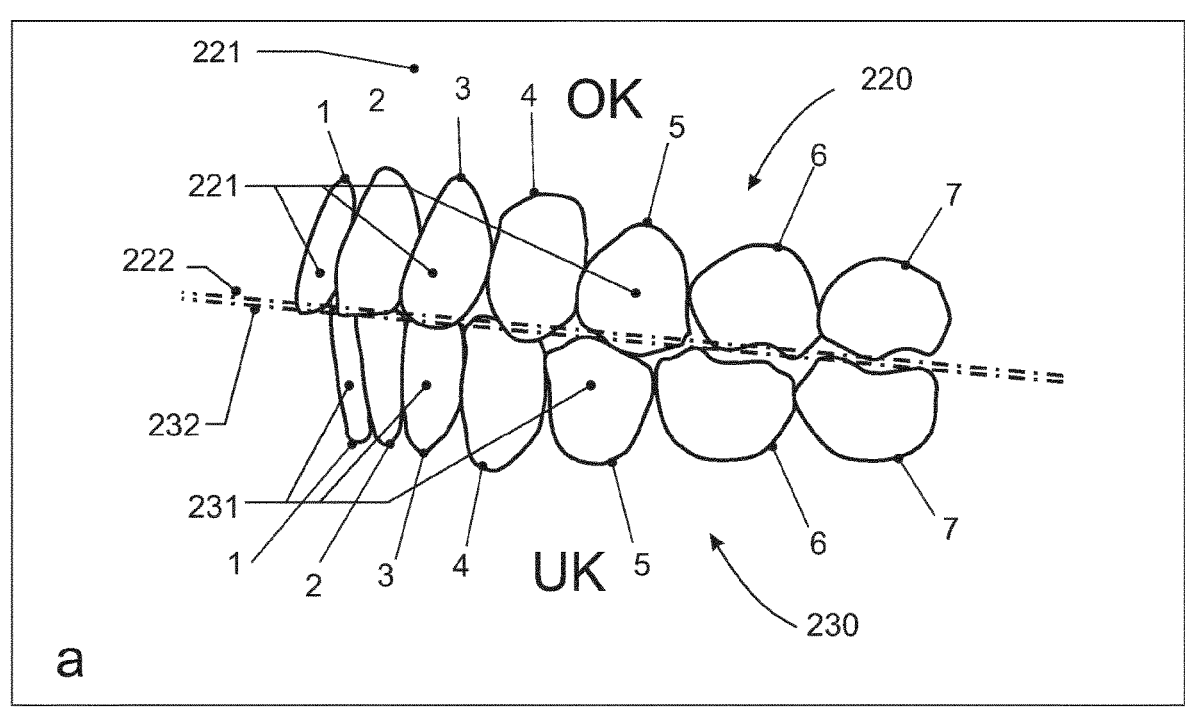
Figure 2:
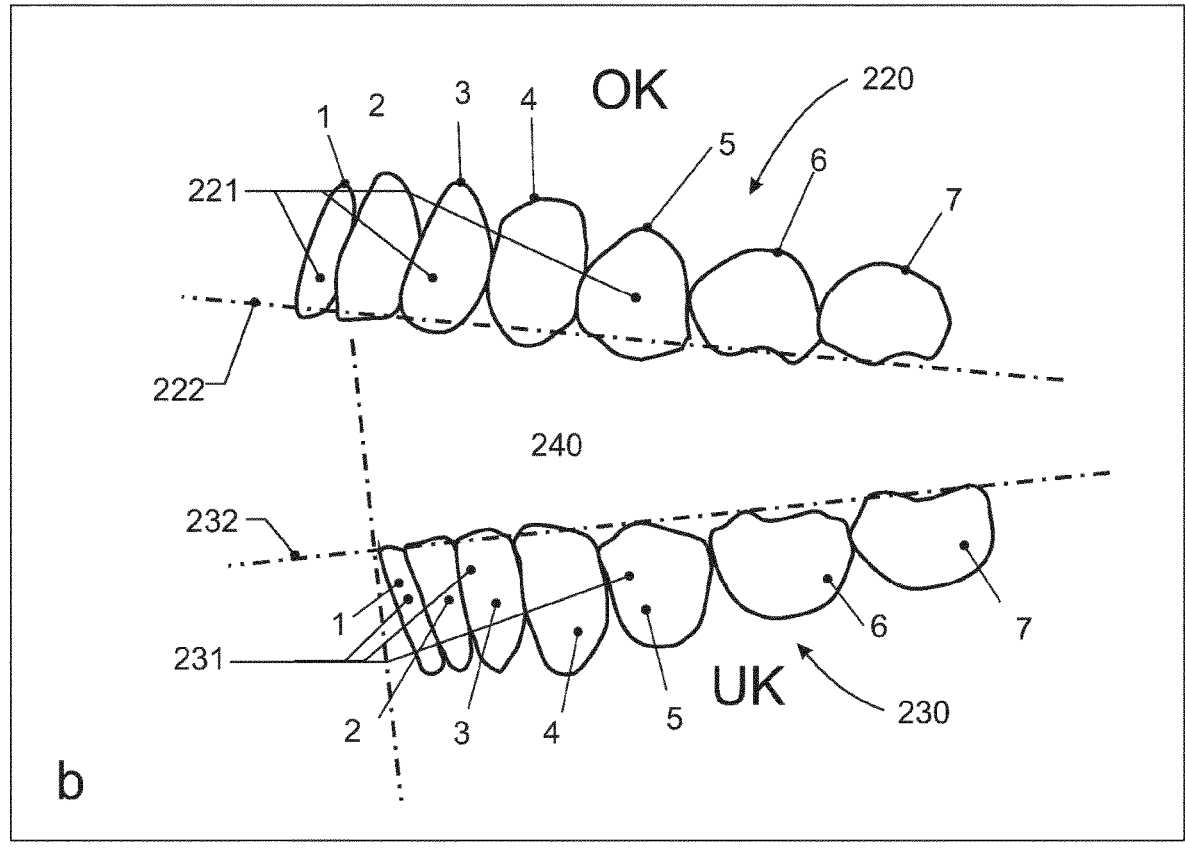

FIG. 2 shows the dental arches 221, 231 of the upper jaw 220 and of the lower jaw 230, closed at the top (FIG. 2*a*) and open at the bottom (FIG. 2*b*).

Figure 3:
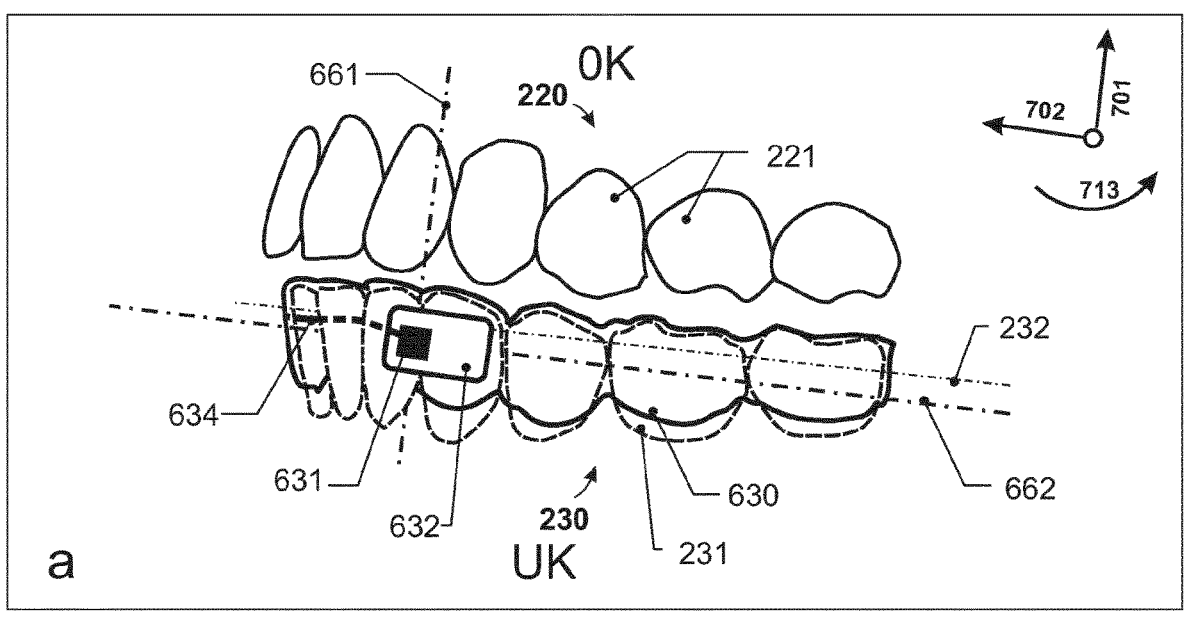
Figure 3:
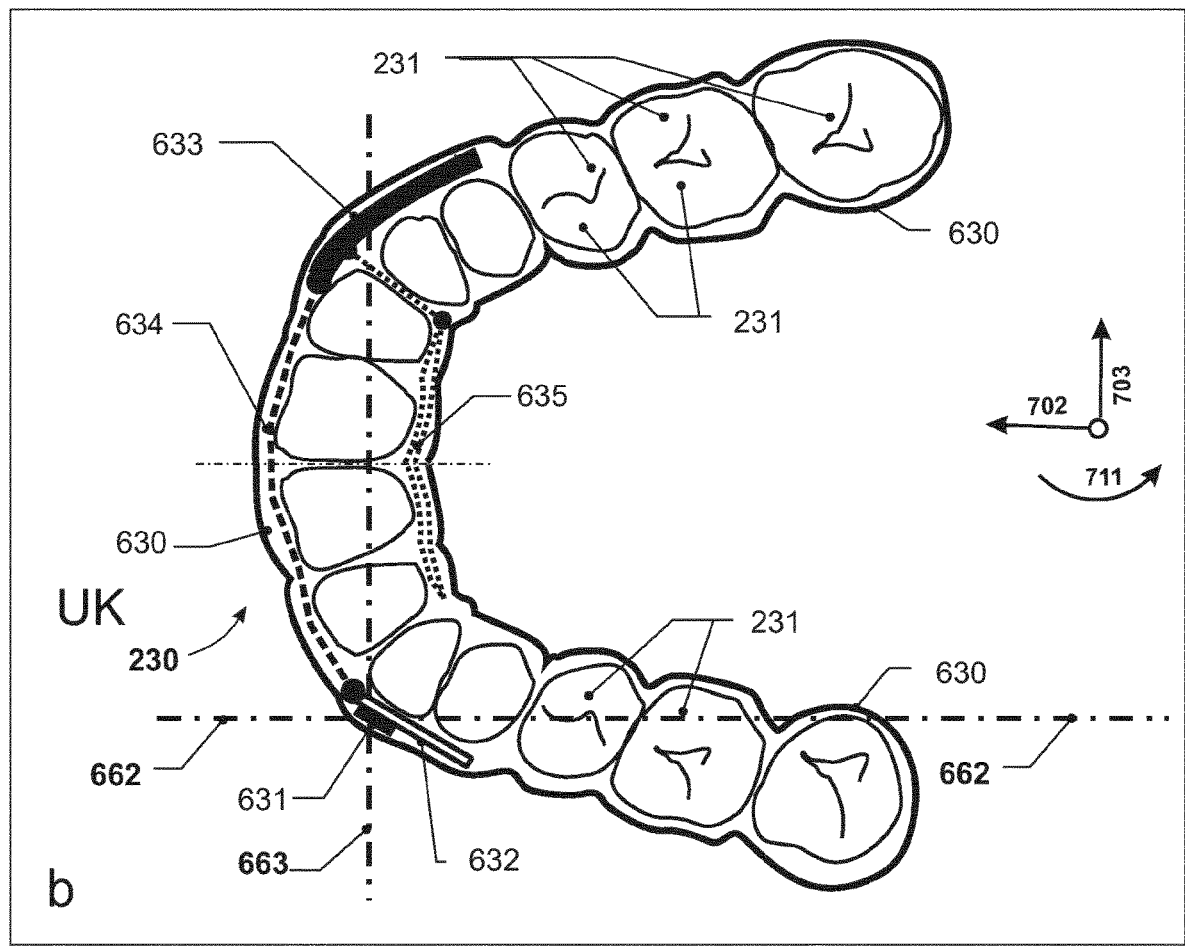

FIG. 3 shows at the top (FIG. 3*a*) the side view of the dentition with a subsystem 30 inserted only in the lower jaw, which subsystem 30 is integrated in the fastening device 630 and is fastened to the lower dental arch 231.

Figure 4:
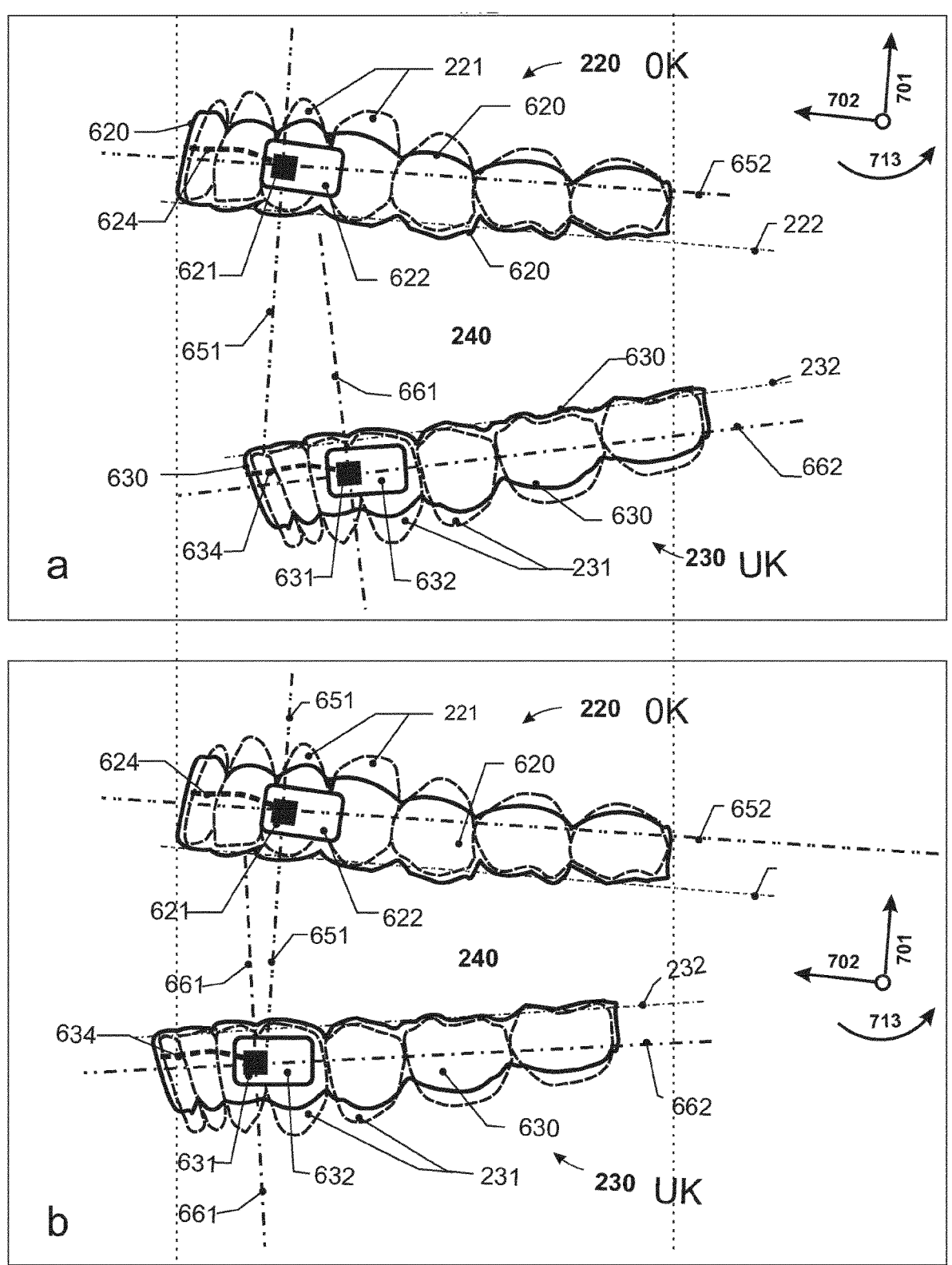

FIG. 4 shows the upper jaw 220 with device 620 and sensor element 621 and the lower jaw 230 with device 630 and sensor element 231 in two open positions: at the top the lower jaw is drawn back, and at the bottom the lower jaw is pushed forward.

Figure 5:
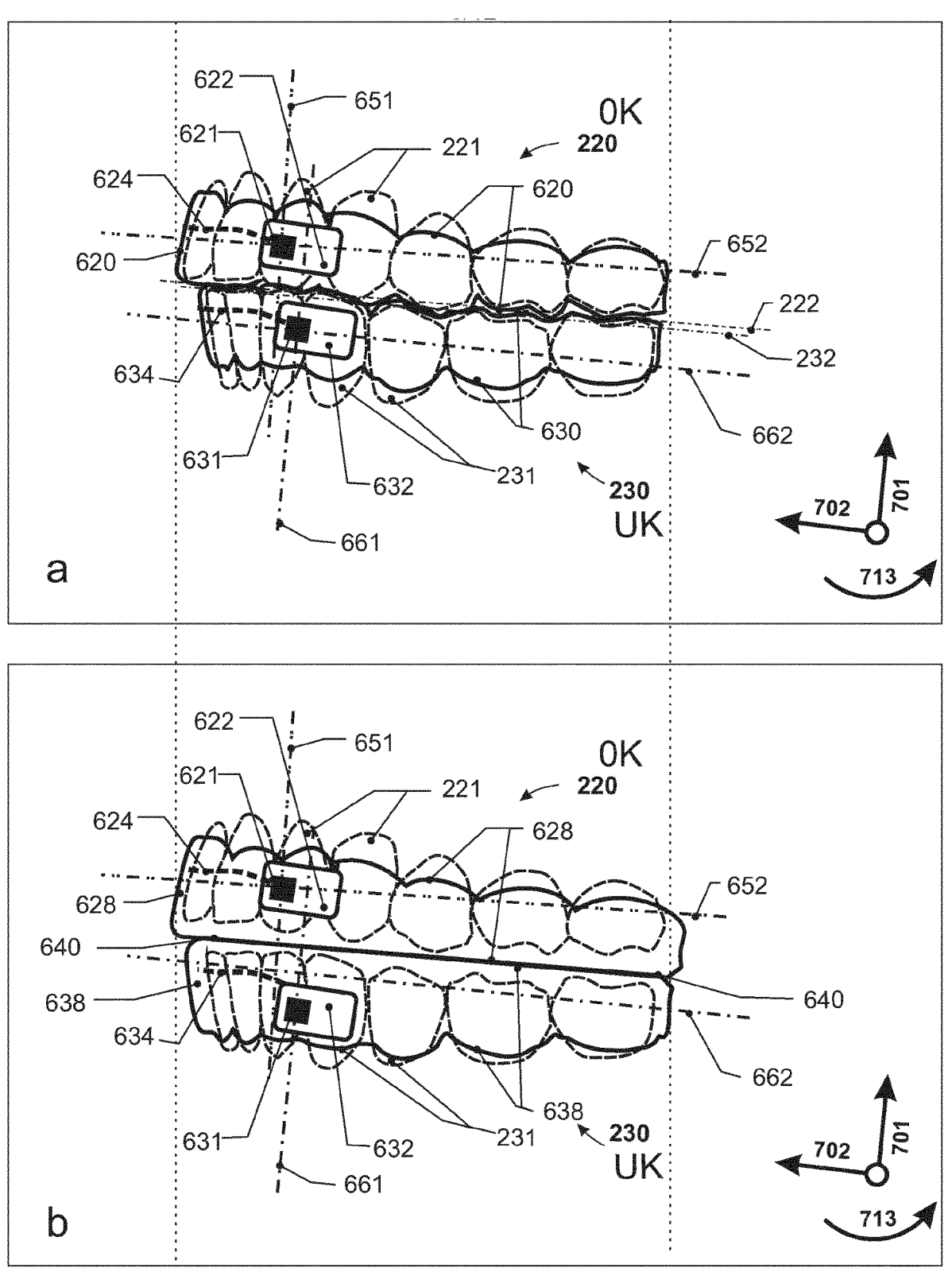

FIG. 5 shows metrologically effective dental devices with upper jaw sensor 621 and lower jaw sensor 631, which each have further components 622 and 632; at the top (FIG. 5*a*) a variant with retentions, cusps and fissures similar to aligner splints, and at the bottom (FIG. 5*b*) with a planar sliding surface between upper jaw part and lower jaw part.

Figure 6:
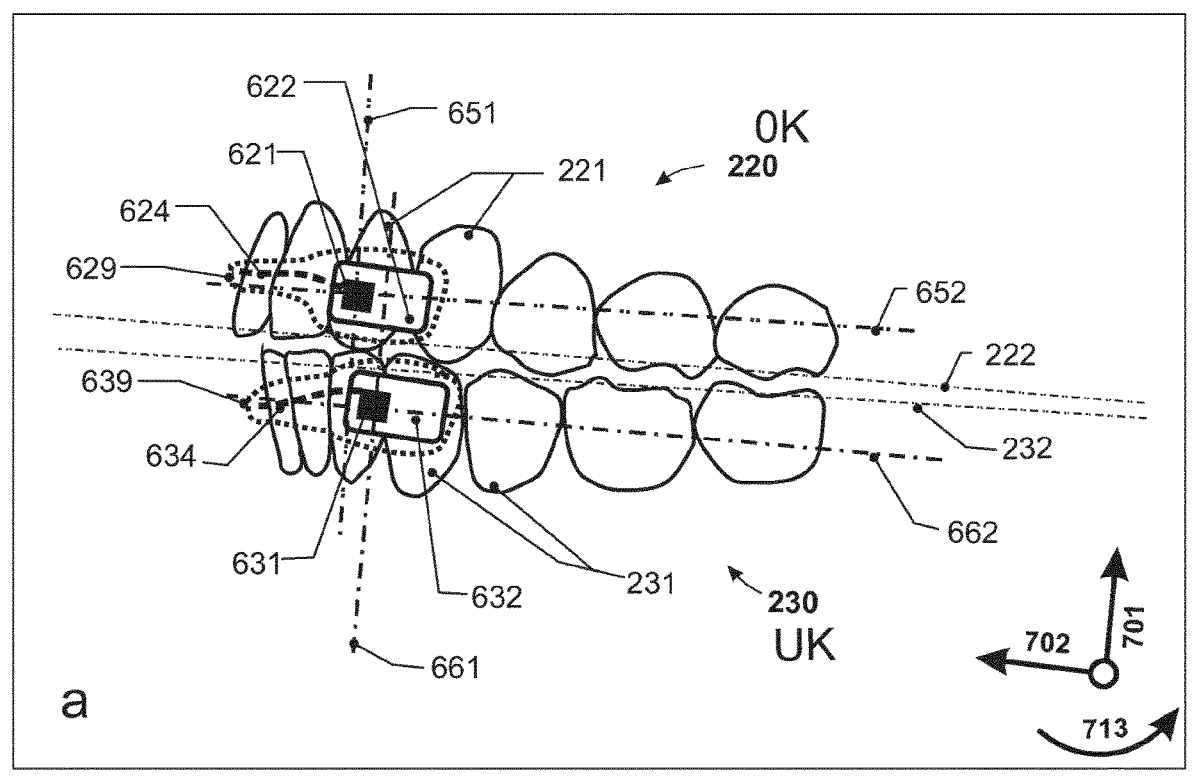
Figure 6:
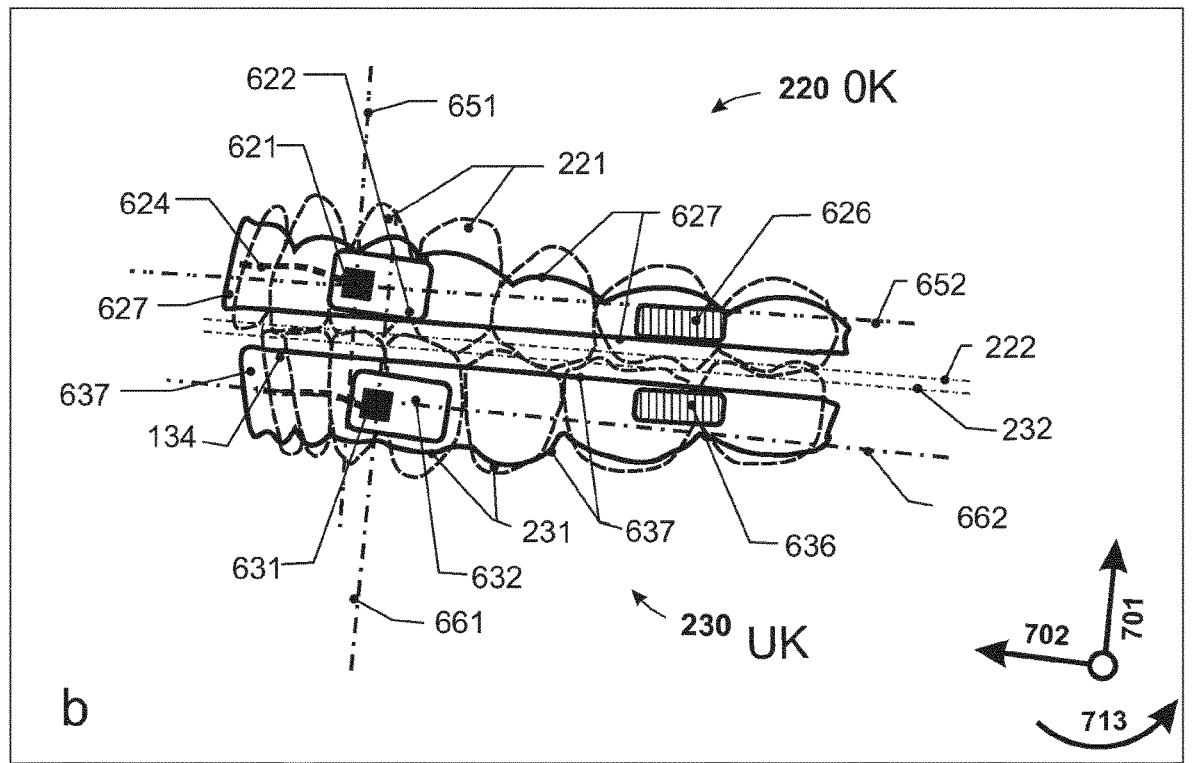
Figure 7:
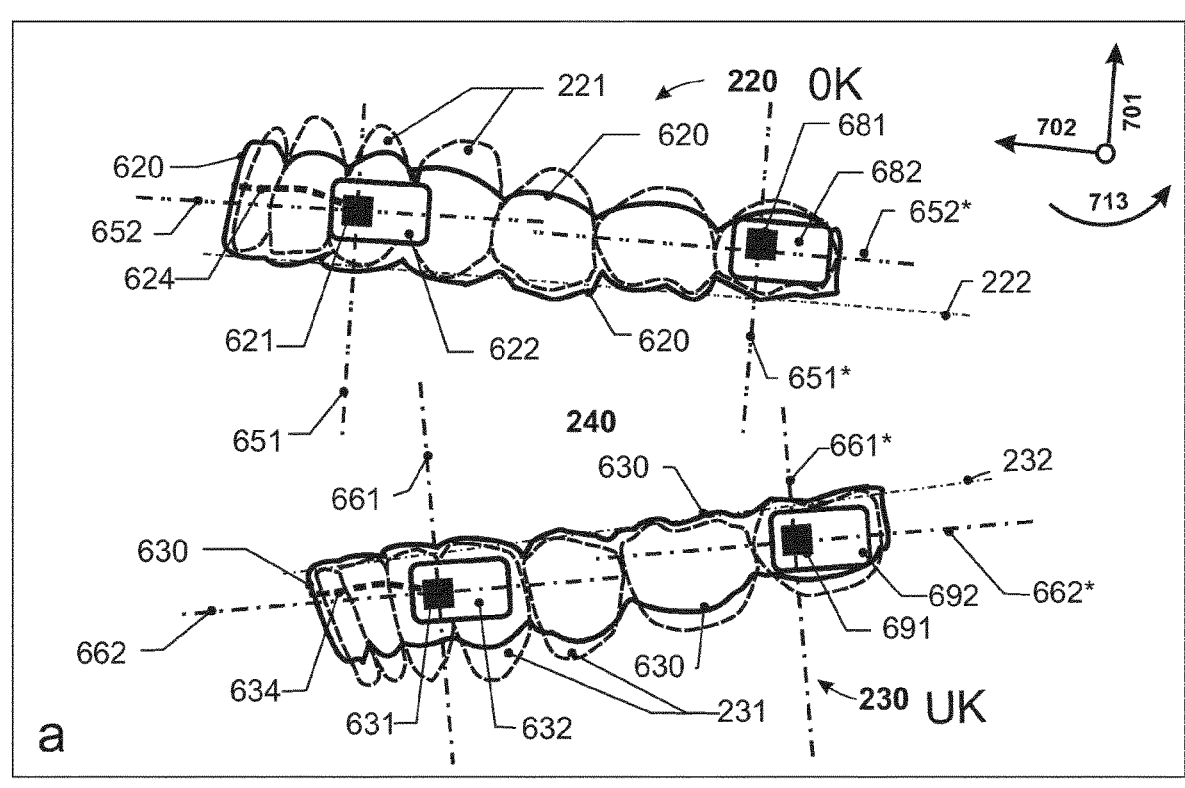
Figure 7:
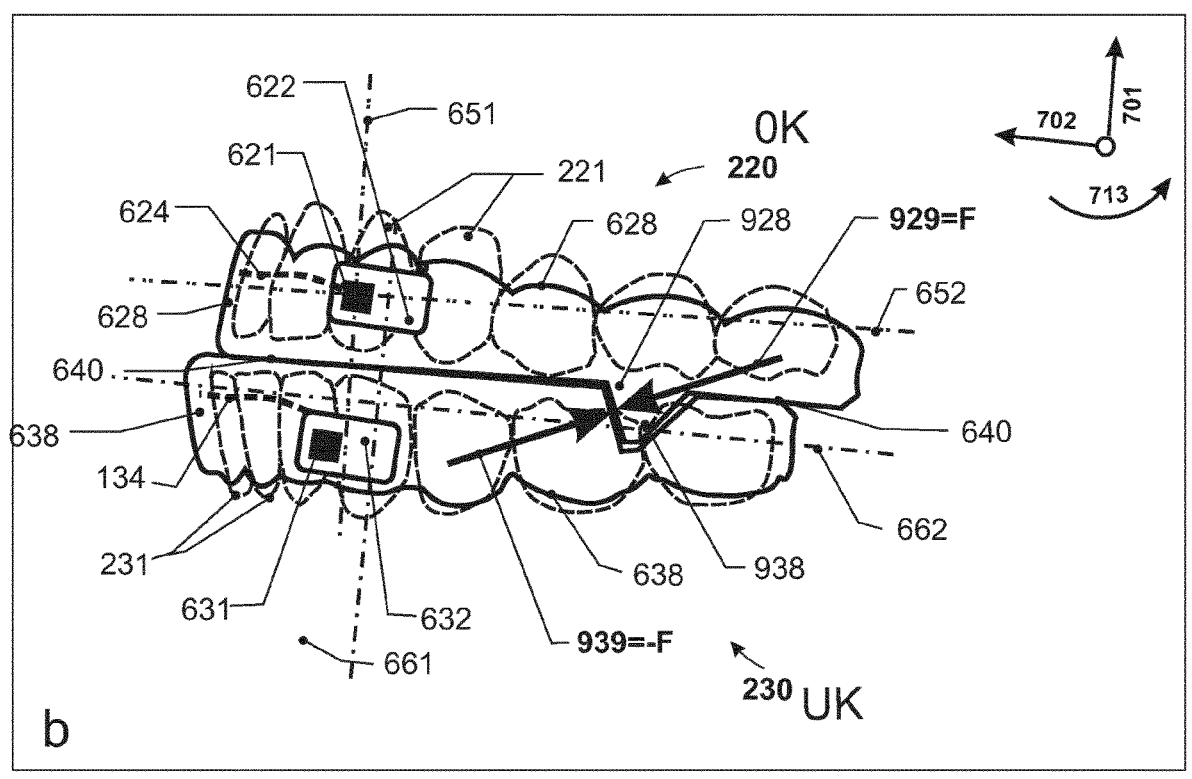

FIG. 6 shows further variants in order to be able to measure the occlusion in an unimpeded manner; in FIG. 6*a* a version with locally affixed sensory elements 621, 622 and 631, 632, and in FIG. 6*b* a variant with non-occlusal fastening devices which not only contain the sensor elements but additional calibration devices 626 and 636.

FIG. 7*a* shows further variants with subsystems for the upper jaw and lower jaw, each with two sensors of different sensitivity ranges, 621 and 681, preferably configured for contact bite and near distance or wide opening and far distance or vice versa, the same on the lower jaw.

FIG. 7*b* shows a protrusion splint for anti-snoring therapy with an integrated sensor system; subsystem 621, 622 at the top, subsystem 631, 632 at the bottom.

Figure 8:
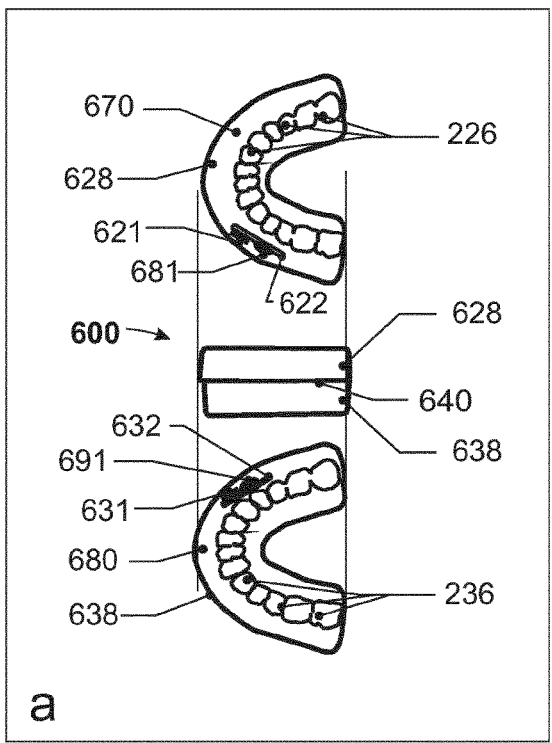
Figure 8:
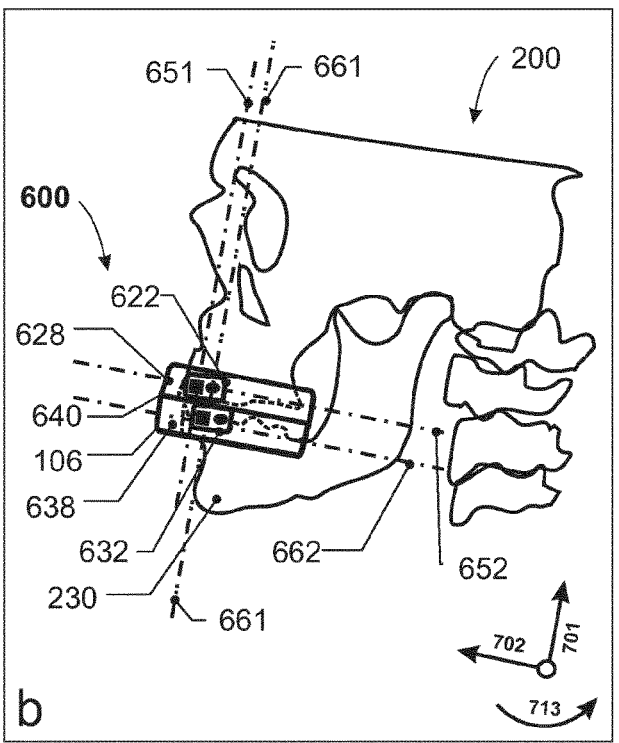
Figure 8:
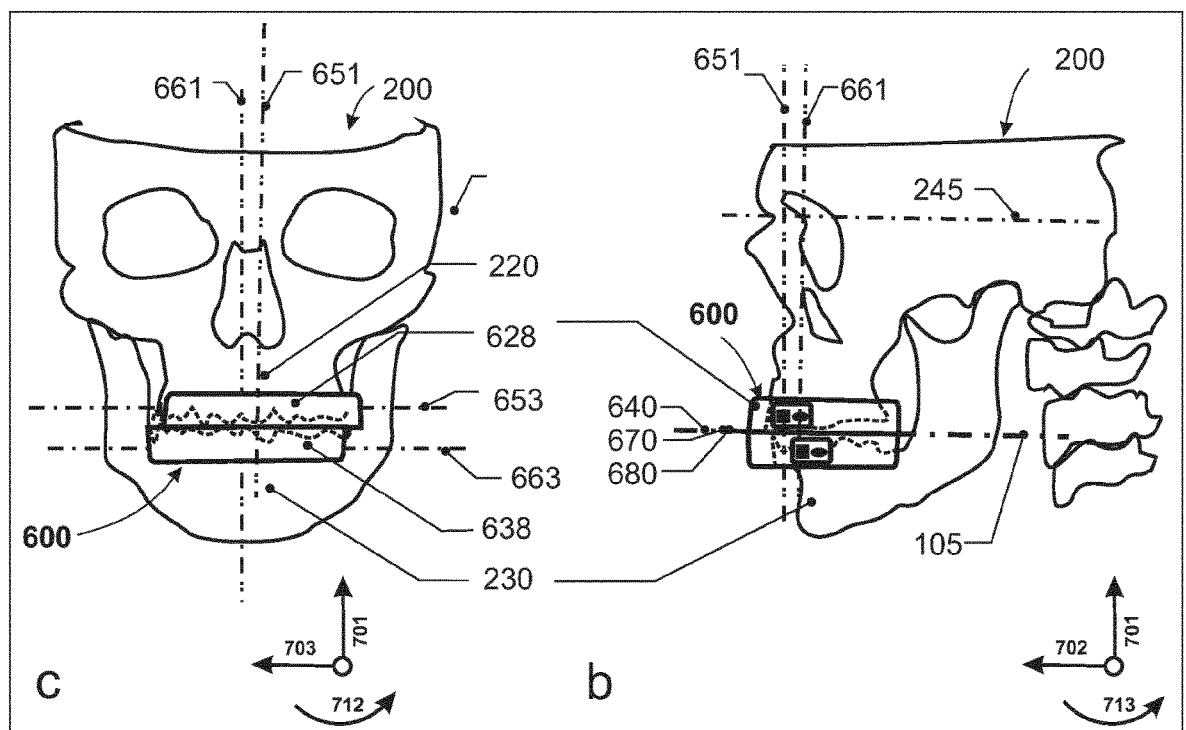

FIG. 8 shows the system used for movement detection especially on a solid biomechanical system 600 with upper jaw part 628 and lower jaw part 638. The special feature of the device 600 is that, under contact, it permits only translations in the plane and rotation around the plane normal. This can be used for therapeutic purposes but also serves to calibrate the sensory system 100.

Figure 9:
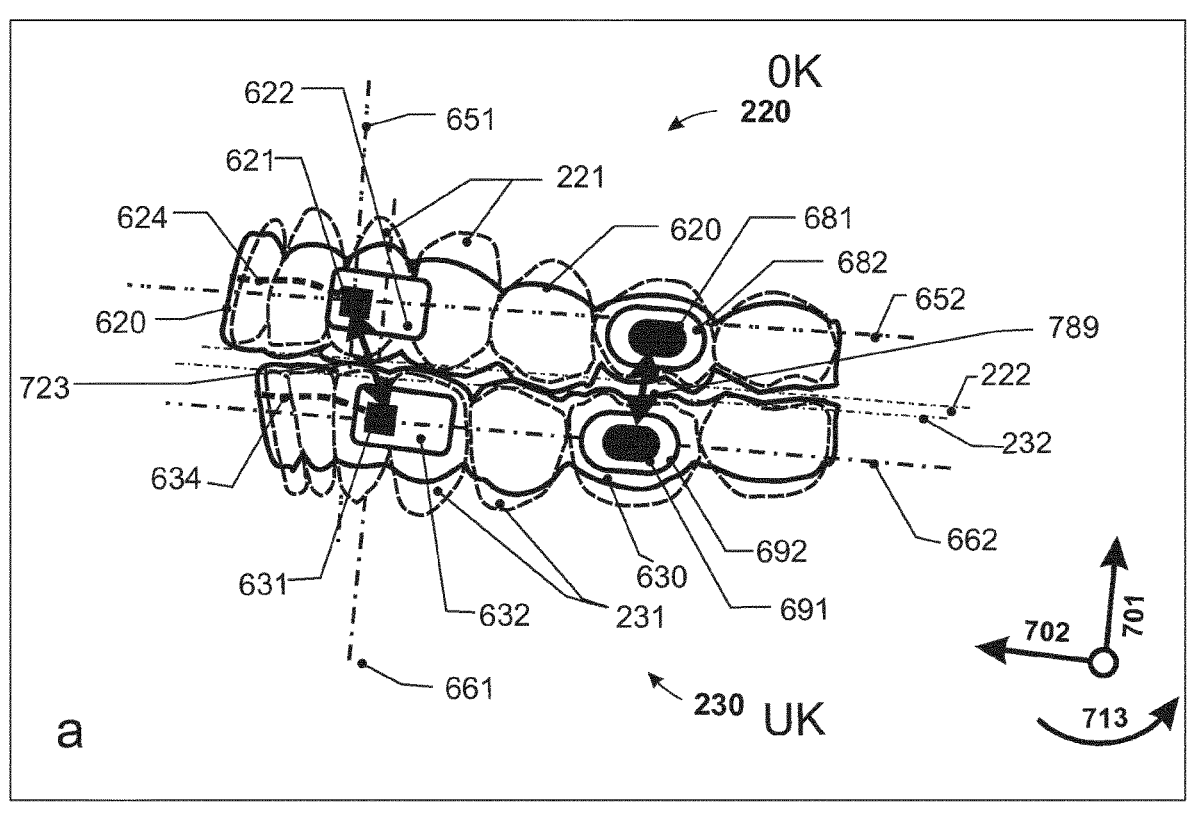
Figure 9:
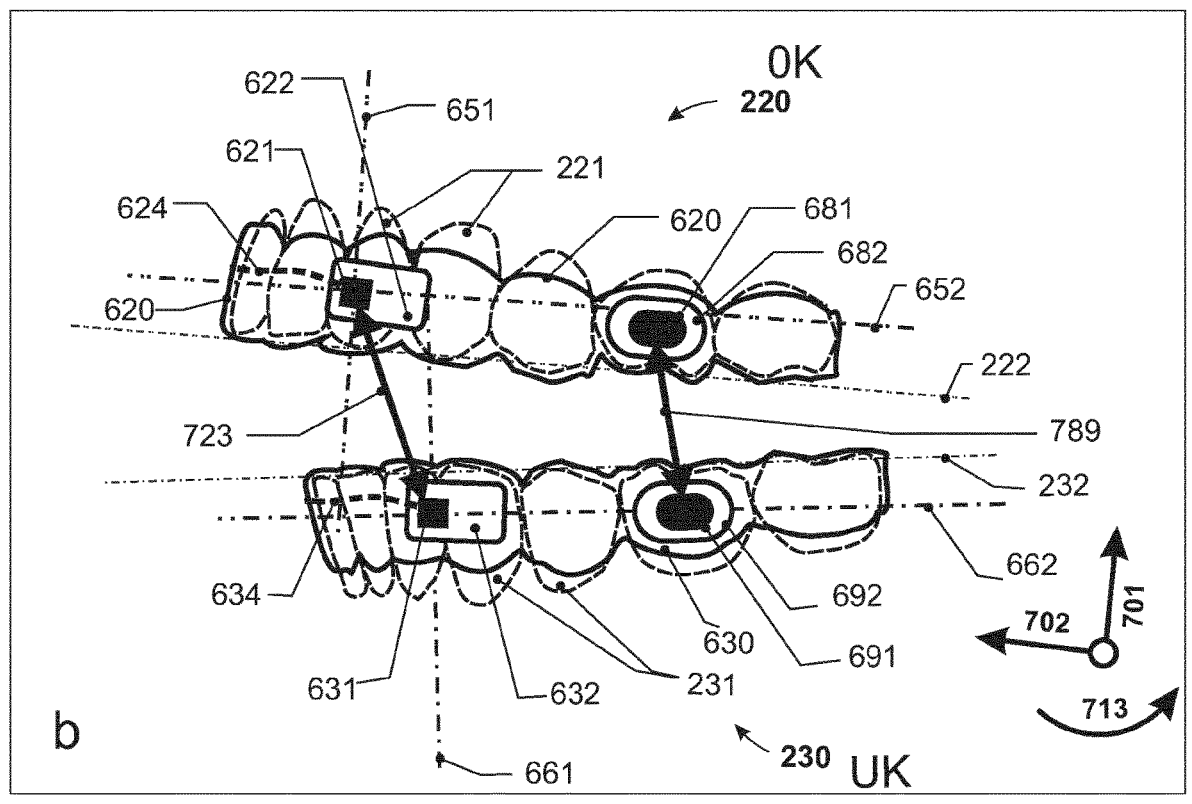

FIG. 9 shows the formation of sensor groups between upper jaw and lower jaw, wherein the sensorially effective interaction 22 and 82 is built up between sensor elements configured for this purpose; FIG. 9*a* at the top shows the mouth closed, and FIG. 9*b* at the bottom shows the mouth opened, with the chin slid back, in particular a snoring position.

Figure 10:
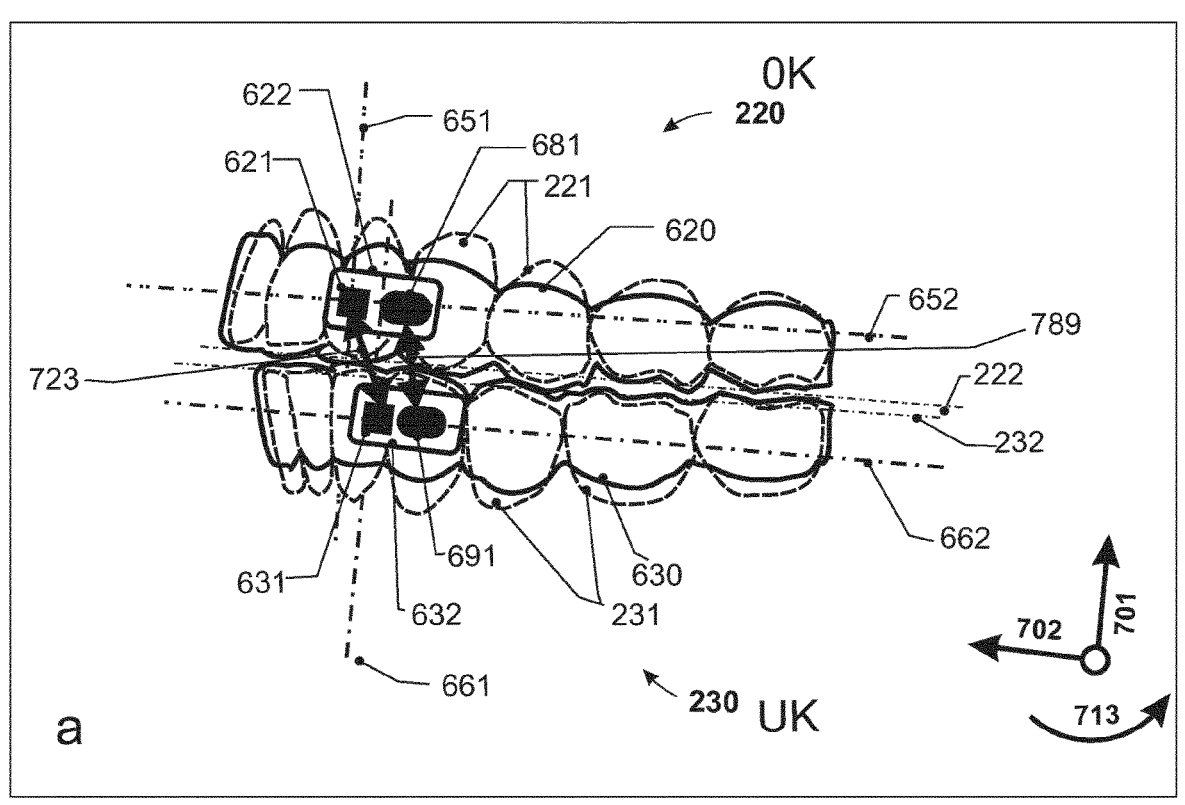
Figure 10:
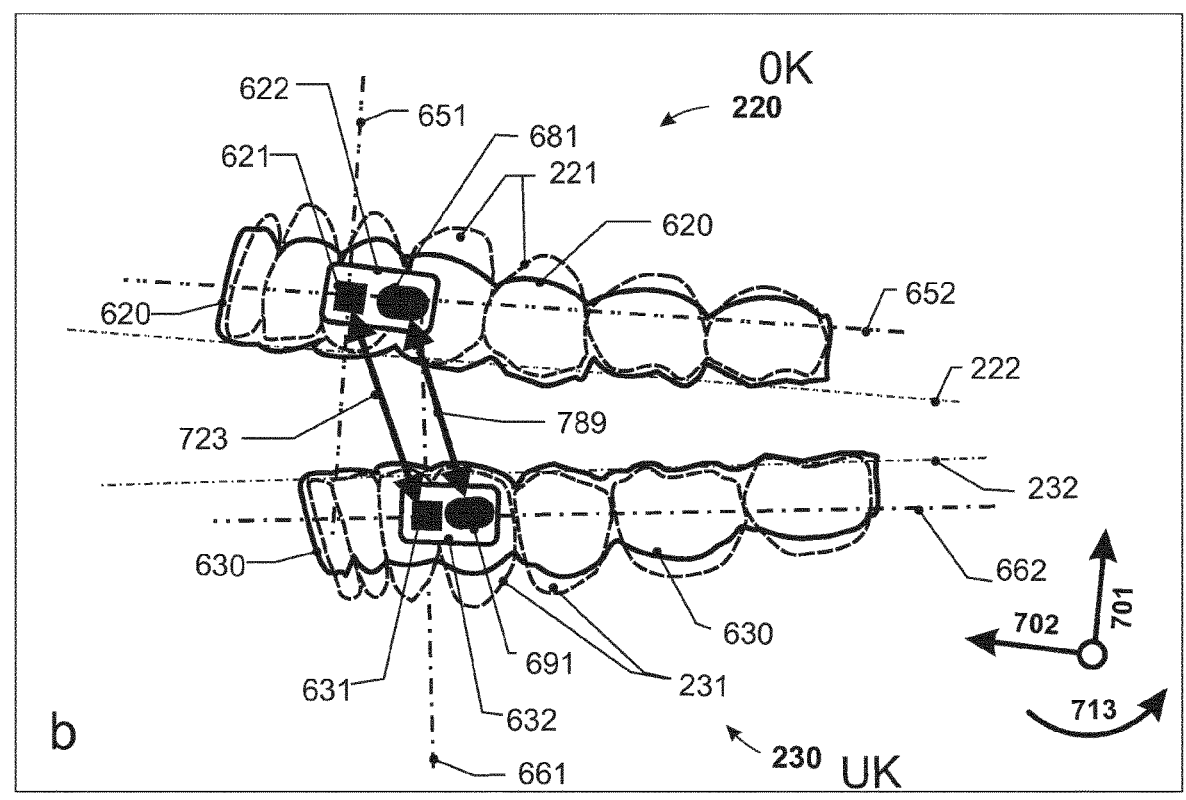

FIG. 10 shows the direct integration of two sensor groups in a sensor component 622 with sensors 621 and 681 in the upper jaw and a component 632 with sensors 631 and 691 in the lower jaw. The sensor groups are 621, 631 and 681, 691. The sensor group here consists of a sensor 621 S_motion for the detection of extensive movements, for example by an integrating inertial sensor system combined with a locally more accurate measuring sensor system 681 S_calibration.

Figure 11:
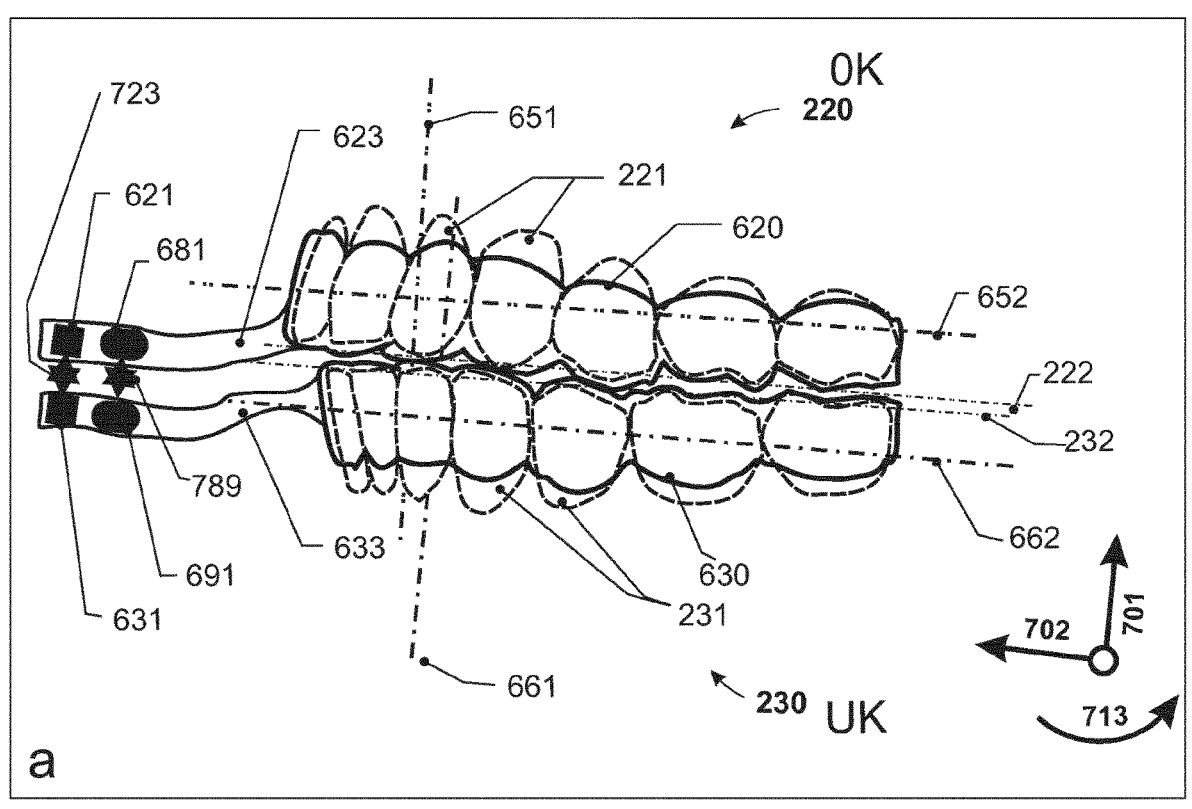
Figure 11:
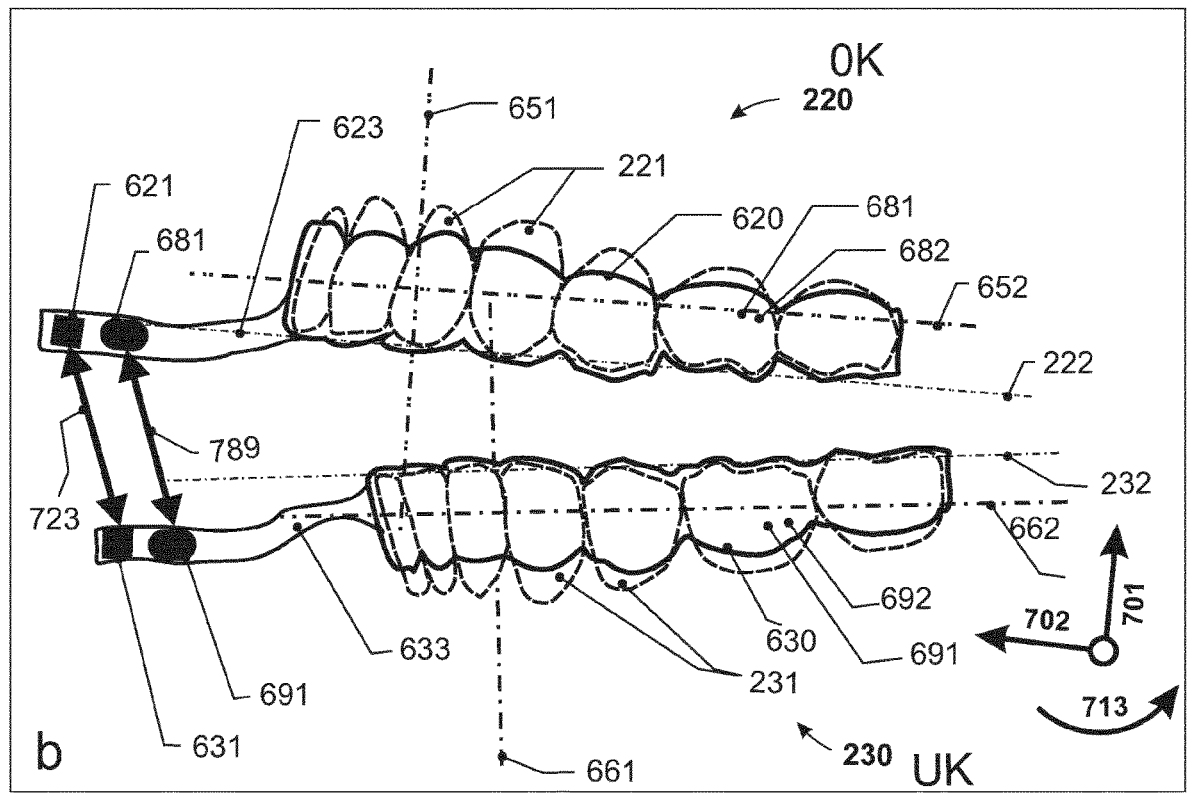

FIG. 11 shows a variant for mainly short-term use with a fastening device 620 extended forward out of the mouth with 623 on the upper jaw and a fastening device 630 extended forward out of the mouth with 633 on the lower jaw, and the sensor elements 621 and 681 at the top and 631 and 691 at the bottom on the extension. The sensor groups are 621 and 631 with interaction 22, and 681 and 691 with interaction 82.

Figure 12:
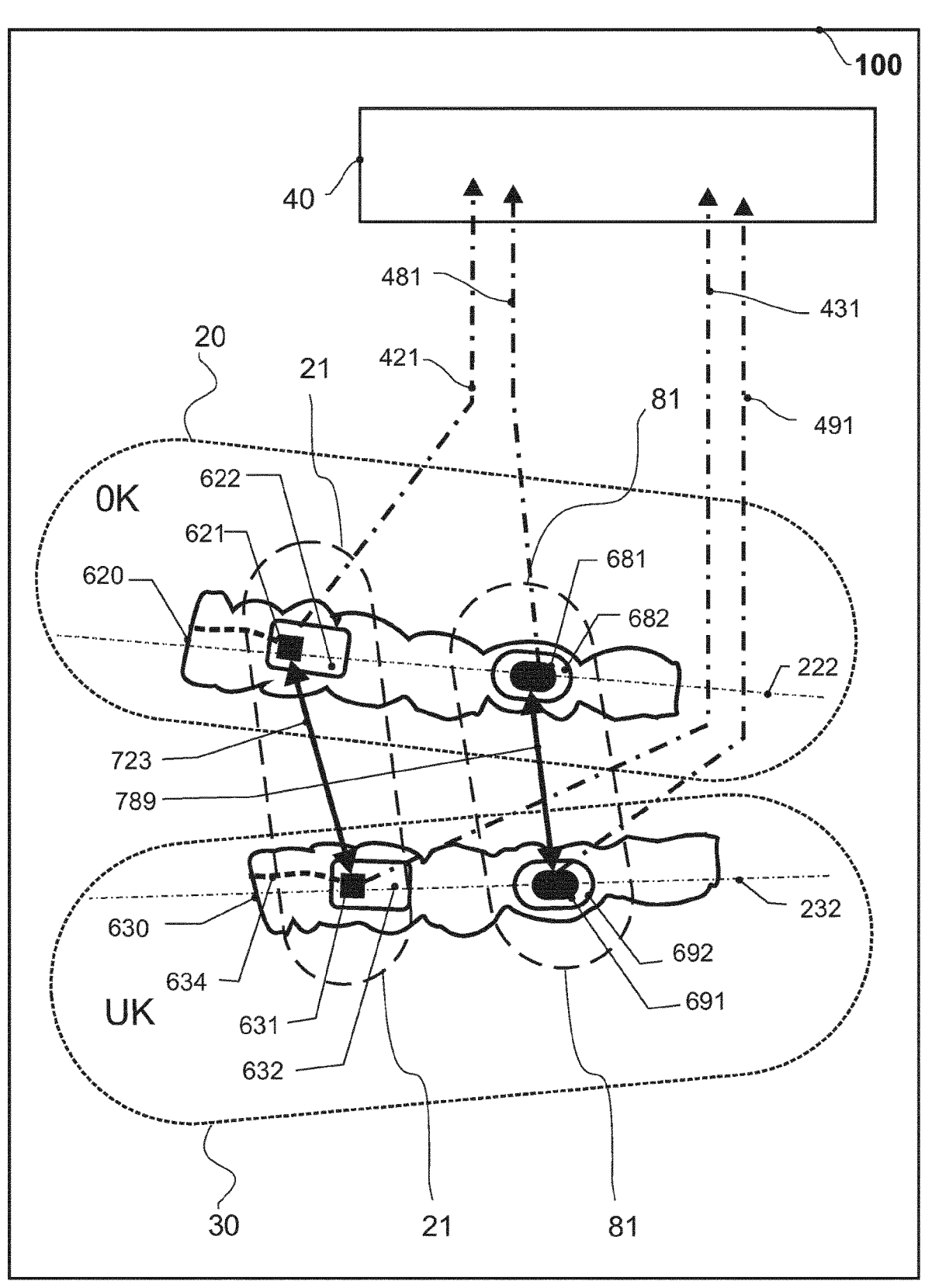

FIG. 12 shows the overall sensor system 100 with subsystem 20 for the upper jaw and subsystem 30 for the lower jaw. The sensor group 21 consists of sensor elements 621 and 631. The sensor group 81 consists of sensor elements 681 and 691. Preferably, one sensor group is configured in particular for the detection of the near distance and another sensor group for the detection of the far distance and the orientation in space.

DESCRIPTION OF SOME COMPONENTS AND CONCEPTS

The system for movement detection comprises a system for detecting the relative movement of body parts, the system having at least two subsystems, i.e. a first subsystem and a second subsystem, wherein the first subsystem is designed to be fastened to a first body part, for example the upper jaw, or to a body region rigidly connected to the upper jaw, such as the skull, and the second subsystem is designed to be fastened to a second body part, for example the lower jaw, wherein the first body part and the second body part are movable relative to each other, and wherein the system comprises a movement sensor system and a calibration sensor system, wherein the movement sensor system is designed to detect the relative movement or relative positions of the first body part and of the second body part across a movement range, for example by generating data from which the movement trajectory or course of the relative movement of the first body part and of the second body part can be obtained or is obtained, and the calibration sensor system is designed to determine the relative position of the first body part relative to the second body part if (for example only if and/or always if) the first body part and the second body part are arranged relative to each other, preferably close to each other, in a calibration region.

In a preferred embodiment, the calibration sensor system and/or the movement sensor system is designed to determine the relative position in 6 degrees of freedom (six coordinates: three in rotation, three in translation). In another embodiment, it is designed to compare the current relative position, obtained by means of the calibration system, with a relative position obtained preferably at the same time by means of the movement sensor system, in order to carry out a calibration adjustment.

In a preferred embodiment, the system is designed such that, in particular if or only if the calibration adjustment shows that the compared relative positions are different, the system is designed to transfer the current relative position, determined by means of the calibration sensor system, to the movement sensor system, such that the movement sensor system can use the current relative position as a starting point for the further movement detection.

In a preferred embodiment, the positions or relative positions are always overwritten when the calibration system delivers measurement values within the calibration region. In another exemplary embodiment, only if the relative positions are classified as different, if the deviation in at least one coordinate is greater than or equal to 10 micrometers or more than 1 millionth of the measuring region, in particular if or only if the calibration adjustment shows that the compared relative positions are different, based on the current relative position, the trajectory determined by means of the movement sensor system is modified before the calibration adjustment, such that the trajectory leads through the current relative position.

In a particularly preferred embodiment, the system is designed such that the modification comprises a smoothing of the trajectory, in particular limited to a region close to the current relative position. Furthermore, it is designed such that the modification adapts the trajectory to a natural movement.

In a further development, the calibration sensor system and/or the movement sensor system can be determined to determine the movement trajectory or the trajectory in 6 degrees of freedom (six coordinates: three in rotation, three in translation). For this purpose, the system is designed to use data, obtained by means of the calibration sensor system, to check data obtained by means of the movement sensor system. The movement range comprises all of the relative positions that the first and the second body part can assume relative to each other, in particular the relative positions in the normal sequence of movements. The calibration range is particularly preferably a real subset of the movement range. Moreover, the calibration range comprises the occlusion position between upper jaw and lower jaw and/or a region adjacent to the occlusion position. Particularly preferably, the calibration range, especially in terms of volume, is less than or equal to one of the following percentages of the movement range: 30%, 25%, 20%, 15%.

In a particularly preferred embodiment, the calibration sensor system has, in the calibration range, a measurement accuracy which is greater than the measurement accuracy of the movement sensor system, in particular in the movement range and/or in the calibration range. In the calibration range, the calibration sensor particularly preferably has a resolution which is at least 5 times as high as the average resolution of the movement sensor in the movement range.

The first subsystem preferably has a subsystem carrier which is designed for fastening to the first body part. Preferably, the second also has a subsystem carrier which is designed for fastening to the second body part. The first system carrier and/or the second system carrier is designed to function as a carrier for at least one component of the calibration sensor system and/or of the movement sensor system. The calibration sensor system has at least one calibration sensor.

Further advantageous refinements result from the features mentioned in the claims and in the aspects, which are hereby explicitly incorporated by reference into the description of the exemplary embodiments.

System

The system 100 preferably comprises at least one measuring system for at least six degrees of freedom of position and movement, in particular three translational degrees of freedom in the three-dimensional spatial position of a body and three rotational degrees of freedom of the angular position of a body, which has to be defined in addition to the position in order also to establish the spatial orientation of the body. In FIG. 1 and in FIG. 3 to FIG. 11, the degrees of freedom of movement are marked symbolically by an axis system which shows two orthogonal translation axes 701, 702 in the plane of the drawing and a rotation axis 713 perpendicular thereto. The spatial translation axes are labeled by the reference signs 701, 702, 703, the rotation axes by the reference signs 711, 712, 713. In everyday language, the three spatial directions are upward 701, forward 702 and to the right 703 toward the right cheek. FIG. 1 shows a skull, as seen e.g. in section in a DVT X-ray image, with the teeth. The lower jaw 230 articulates in the temporomandibular joint, which is here a biomechanical, muscularly guided rotary sliding joint that allows rotation and translation. Rotations take place not only about the axis 713 running transversely from left to right (see FIG. 1a), but also about the vertical axis 701, e.g. during grinding movements of the lower jaw. From this point of view, it makes little sense that a number of publications speak of determination of a hinge axis of the temporomandibular joint, because a hinge axis does not exist in the jaw any more than it does in the knee joint, unless a mechanical hinge is installed in place of the natural joint. From an anatomical point of view, however, the transverse axis can be drawn through the two centers of curvature of the temporomandibular joint condyles in the three-dimensional X-ray image.

However, when detecting the movement with the aid of the proposed device, it will then be seen that this anatomical axis through the condyles to the right and left represents the rotation axis of the temporomandibular joint only in the highly unlikely case of pure rotation without sliding.

A component of the proposed system 100 that is preferably present is the subsystem 20 for the movement detection of one body part, in the exemplary embodiment the upper jaw 220. This subsystem 20 also detects the movement of the head 200 (see FIG. 1). The detection takes place by means of a sensor subsystem 621, 622, 681 (see FIG. 9) which is fastened to the upper jaw. The fastening is preferably effected using a fastening device 620 which, in particular for short-term measurements, can have an extension 623 to the outside. The sensor subsystem can also be affixed directly to the teeth, but the relative movement of the teeth to the jaw then has to be taken into account. The subsystem for detecting the movement of the upper jaw is supplied by an energy element and, with an information element or a storage device, can optionally store, process and/or transmit the information 421, 481 from the sensors 221, 281.

A further component of the system 100 that is preferably present is the subsystem 30 for the movement detection of the other body part, in the exemplary embodiment the lower jaw 230. This subsystem 30 moves relative to the subsystem of the upper jaw OK (see FIGS. 8a and 8b). The detection takes place by means of a sensor subsystem 631, 632, 691 (see FIG. 9) which is fastened to the upper jaw. The fastening is preferably effected using a fastening device 630 which, in particular for short-term measurements, can have an extension 633 to the outside. The sensor subsystem can also be affixed directly to the teeth in the lower jaw, but the relative movement of the teeth to the jaw then has to be taken into account. The subsystem for detecting the movement of the lower jaw is likewise supplied by an energy element and, with an information element, can optionally store, process and/or transmit the information 431, 491 from the sensors 231, 291.

The overall system 100 detects the position and movement of the upper jaw OK and thus of the skull 200 and also the position of the lower jaw 230 or, alternatively, directly the relative position of the lower jaw 230 with respect to the upper jaw 220, such that both the upper jaw position and the lower jaw position are detected.

Sensor Groups

The overall system 100 has, inter alia, the object of determining the six-dimensional relative position or relative movement, i.e. 3 dimensions in translation and 3 dimensions in rotation of the two body parts. The example concerns the six-dimensional relative position of the lower jaw 230 in relation to the upper jaw 220. For this purpose, it is not only possible to determine the two spatial positions of upper jaw and lower jaw and to derive the relative position therefrom. In a particularly preferred embodiment, the components of the subsystems 20 (OK) and 30 (UK) can be used to create sensor groups that interact with one another between the subsystems 20 and 30. The interaction is preferably between mutually opposing components as in FIG. 12. Interaction 22 between 621 and 631 and/or interaction 82 between 681 and 691. Particularly preferred interactions are magnetic ones between magnets and magnetic field sensors or optical ones between optical emitters or optical structures and optical sensors. The elements that form an interaction represent sensor groups 21 and 81 (see FIG. 12). The sensor groups 21, 81 are additionally evaluated or can preferably also be evaluated for determining the relative movement. Sensor groups in the sense of the formation of measurement values also exist when the sensorially effective components 621, 681 or 631, 691 are combined in one assembly and are spatially closely adjacent (see FIG. 10 and FIG. 11).

Position Sensor

In addition to the sensor system for movement detection and/or the sensor system for calibration, the system can comprise a position sensor (not explicitly shown) that determines the 6DOF position of the body, for example on the basis of the upper jaw or the skull in real space. The absolute position of the head, for example, can thus be precisely determined and linked to other events or peculiarities that are determined on the basis of relative position data.

Near Distance and Far Distance

In a preferred embodiment, at least the subsystem for the upper jaw 220 has a six-dimensional detection of the subsystem 20 in space and, in addition, the overall system 100 has at least two sensor groups 21, 81 which have different detection properties as regards distance, measuring range or resolution (see FIG. 12). As soon as one of the systems is an integrating system, the challenge arises to compensate for the integration errors that arise in the case of complex and, in particular, sometimes very slow or very rapid movements. For this purpose, the system comprises special components for the near distance, which are configured to measure a short distance with a high degree of accuracy of preferably two to two hundred micrometers by forming sensor groups with the opposite side. Preferably, other components 31, 91 are additionally configured to measure at greater distances with a particularly large range of movement and yet with sufficient accuracy, but less precisely than the components for the near distance.

A preferred embodiment comprises a first sensor group 21 composed of at least two metrologically effective parts 621, 631 for the near distance and in particular measures the almost complete approach of the lower jaw to the upper jaw precisely and also the six-dimensional relative movement and relative position when biting firmly. The same sensor group 21 or a second sensor group 81 for the remote distance has metrologically effective components 81, 91 which are configured in such a way that they detect slow and rapid movements to the full extent at greater distances, albeit with less resolution and accuracy and possibly also with certain integration errors, as occur in the case of integrating inertial sensors.

The highest precision of the first sensor group 21, 621, 631 for the near distance is preferably set in such a way that it comprises the position ranges between direct tooth contact and a slight opening of a few to ten millimeters. The highest precision of the second sensor group 81, 681, 691 for the far distance is preferably set in such a way that it comprises the adjoining position ranges between a slight opening of a few to ten millimeters and the maximum opening of the mouth or the maximum distance of the body part that can be detected. Through the joint evaluation of the two sensor groups 21, 621, 631 for the near distance and 81, 681, 691 for the far distance, the entire position and movement range is detected with the greatest possible precision, by the near distance being detected by the sensor group 21, 621, 631 and the far distance being detected by the sensor group 81, 681, 691. The assignment of the sensor groups 21, 621, 631 and 81, 681, 691 to near distance and far distance can of course also be interchanged.

Recalibration

The system and the metrologically effective components and sensor groups are preferably calibrated at the start of a measurement. If the system 100 is worn for long periods in the mouth, further calibration measures are also provided which together lead to the accuracy that is achieved overall. For this purpose, the overall system 100 has at least one device 40 and a method 400 for recalibrating the relative position, in the exemplary embodiment, between upper jaw OK and lower jaw UK.

The device 40 for recalibration preferably has information interfaces 421, 481 491, 431 to the sensor elements 21, 81, 91, 31 and comprises memory elements for calibration values, memories for information and/or measurement values and processor devices for information processing, preferably also for calculating the six-dimensional position data for upper jaw and lower jaw.

Method

The recalibration of the determined relative position between lower jaw and upper jaw is carried out or alternatively triggered by a signal as soon as the lower jaw is located or moves in the region of the near distance relative to the upper jaw and a calibration region within the near distance is reached at which the system detects the relative position. A coordinate value is then assigned to this detected relative position, and the relative relationship between upper jaw and lower jaw is thus recalibrated. In the event that the movement detection in the preceding period has led to deviations from the real state, the currently determined coordinates of the near distance are used and, optionally, the previously generated series of measurement values is preferably corrected by a compensation calculation, such that a uniform and optimally corrected trajectory of the movement results. In particular, the recalibration of the relative position at near distance ensures that there are no measurement value deviations for the lower jaw relative to the upper jaw which would mean an error in the measured relative position during occlusion or chewing movements when the measurement values are reproduced. This ensures that the reproduction of the detected movement and position in six degrees of freedom of the relative position is accurate even if the system 100, which detects the entire movement, generates measurement errors in between, in particular integration errors in the case of inertial sensors. These measurement errors are corrected again at the latest the next time the lower jaw approaches or at the next occlusion.

Application and Use

The proposed system of devices and precisely coordinated method steps is therefore suitable for recording the actual jaw movements, e.g. while eating and exercising or when snoring or grinding teeth, for short, medium and long term use, especially since the recalibration reverts the addition of measurement errors as soon as the lower jaw is moved into close proximity or in occlusion. All of these are functions that previous systems were fundamentally unable to provide for technical reasons.

The evaluation of the movement detection with regard to the relative movement between lower jaw and upper jaw shows in particular that, depending on the type of movement and the stress, the axes of movement can differ dynamically to a very great extent, which indicates very different cartilage loads, depending on the emotions with which the movement is carried out.

Detection

The detection of the position data and movement data of an object, body or body part thus determines the 6-degrees-of-freedom coordinates in such a coordinate system with the coordinates [701, 702, 703, 711, 712, 713]. This coordinate data set is determined for each observation time, and the sequence of coordinates describes the detected movement. In addition, it is possible to specify the size scale of an object, etc., as a result of which the data sets become correspondingly larger. This minimalist 6-degrees-of-freedom coordinate set can also be written differently, e.g. as a seven-dimensional or eight-dimensional vector instead of just with 6 dimensions, the specification then being over-determined. Moreover, the 6 degrees of freedom can of course be limited by mechanical guides, but then only correspondingly limited movements are possible.

In the following, for the sake of clarity, the minimalist 6-degrees-of-freedom notation is used to clearly describe positions and spatial orientations of body parts and objects, insofar as these cannot be assumed to be deformable.

Coordinate Systems

FIG. 1a shows a skull with closed jaw in occlusion from the front. The axis 703 points from left to right in relation to the patient's head, in the image from right to left. The axis 701 points upward. FIG. 1b does not show the coordinate axis 703 because it is perpendicular to the drawing surface. In front, seen from the side, is the coordinate axis 702, which points forward, in the image from right to left in the sectional view seen from the side. The coordinate axis 701 also points upward here. The rotation axes are indicated by the rotating arrows. The mathematical and physical direction of rotation is counterclockwise. The lower jaw 230 thus opens clockwise in FIG. 1c with a positive angle of rotation. If the head is viewed from the other side as in FIG. 1c, the positive direction of rotation is retained, because the coordinate system flips over with the viewing direction. FIG. 7c shows a protrusion position, that is to say, for example, a lower jaw 230 that has been pushed forward and slightly opened by muscle force. In comparison to the upper jaw 220, we therefore have a completely different position than if a hinge movement were to begin in the temporomandibular joint with the rotation axis lying to the rear, as shown in FIG. 7d.

The object of the proposed system can now consist in correctly detecting all movements, rapid changes in position and also lingering sliding movements and always precisely measuring the relative position. The problem now is that there are very slow, creeping movements that would hardly be detected, especially by integrating sensors, and then suddenly once again very rapid movements that could overwhelm the measurement range. In a combination of slow movements and abrupt, rapid movements, the relative position has hitherto not been precisely measurable even with the most modern 6-degrees-of-freedom or 9-degrees of freedom sensors, because their resolution is not sufficient to detect slow sliding movements and to integrate them correctly for precise position or translation. This is due to the technical obstacle of being able to detect small accelerations precisely and still being able to measure large accelerations. The available 6-degrees-of freedom sensor elements, which can be purchased in small modules with an edge length of a few millimeters, will for the foreseeable future therefore have great difficulty with exact position determination after slow movements.

The proposed system 100 preferably comprises at least two devices, at least one of which is coupled to the lower jaw 230, the lower jaw device 630 lying predominantly in the mouth, i.e. within the cheeks and lips, and at least one device 620 coupled to the upper jaw 220, this device also lying within the mouth here, that is to say can be enclosed by the lips. Parts of the device can lie within the dental arch 231, 221 in the tongue and pharynx 240 or also outside the dental arch between the lips or cheeks and the dental arch. At each measurement point in time, each of these devices 620, 630 generates, by sensors 621, 631, a measurement result which can be transformed into a 6-degree-of-freedom coordinate set and thus describes the spatial position of the measurement device 620, 630. There is of course now the question of whether the sensory measurements and calculations are correct and whether the measured 6-degree-of-freedom coordinate sets for upper jaw and lower jaw or other coupled body parts correspond to the spatial directions actually physically existing at this point in time. This is a question of the correct calibration of the sensors and the correct integration of the accelerations and the rotation rates. The proposed technology satisfies these objects better than ever before.

An object to be solved now lies in the medium-term and long-term precise detection of the movement of the body parts and in particular the relative movement, in particular because this is the only way to measure the relative position of the lower jaw with sufficient accuracy during chewing and during snoring. The comparatively precise rotation rate sensor elements do not help here, because the demanding task lies in the integration of the slow translations, which, especially alone, cannot really be achieved precisely using an accelerometer or acceleration sensor. In the particular application in the mouth, the mixture of rapid abrupt movements and slow creeping movements thus leads to serious measurement errors in the relative position if no further measures are taken.

The proposed solution means that the calibration of the relative position of the devices 620 ff and 630 ff can be repeated almost as often as required, especially when in the inserted state, but also e.g. in an articulator in the dental laboratory. For this purpose, it is advantageous if the measurement is carried out with upper jaw device 620, 628, 627 and lower jaw device 630, 637, 638, etc., since there are always no gaps there, especially when the jaw is relaxed.

For the calibration function, the upper jaw device 620, 627, 628 ff has a calibration device 626 which is permanently connected to the upper jaw device. Alternatively, all the device components are permanently connected to the dental arch of the upper jaw. The lower jaw device 630, 637, 638, ff has a matching calibration device 636 which is permanently connected to the lower jaw device. Alternatively, all the device components are permanently connected to the dental arch of the lower jaw.

The two calibration devices (or calibration sensors) 626 and 636 face each other at least in phases, e.g. whenever the lower jaw is relaxed in the resting position or whenever the lower jaw is in occlusion with the upper jaw. This position is now not only detected by the inertially measuring sensors 621, 631, but also by the calibration sensors. The calibration sensors 626, 636 are equipped in pairs so that they allow an exact measurement of the relative position between the two calibration devices 626 and 636. Optionally, several such calibration devices can also be attached per device 620, 630 or per dental arch.

For the sake of clarity, a person skilled in the art should understand at this point that the calibration devices 626, 636 do not have the task of carrying out the complete movement detection. Rather, they have the important task of carrying out the position adjustment, i.e., to put it somewhat crudely in terms of control technology, a zero run, after a preferably predefined series of integration steps, as soon as a detectable calibration position is reached relatively between upper jaw and lower jaw.

Suitable calibration devices work together in pairs in order to determine precise relative positions in comparatively small measurement ranges. To do this, they use a technology selected from magnetic field, electrical field, optical interference, triangulation, pattern recognition, optical center of gravity determination, optical determination of a size feature, angle determination, position determination, or comparable technologies with fine resolution in order to define which relative position between calibration device 626 and 636 is currently actually present.

With the aid of the calibration values from the calibration devices 626 and 636, the coordinate systems or measurement results for all the devices 620 *ff* and 630 *ff* can be corrected in the short, medium and long term.

In a further development, the sensor systems of the device(s) 620 *ff*, 630 *ff* comprise additional gravity sensors, in order in particular to be able to calibrate the vertical direction in the earth's gravitational field. At least the device provided for the upper jaw is preferably equipped with a gravity sensor, such that the vertical direction can be reliably determined for the whole head.

In a further development, the sensor systems of the device(s) 620 *ff*, 630 *ff* comprise additional magnetic field sensors in order in particular to be able to calibrate the north direction in the earth's magnetic field or in another technically generated magnetic field. Gravity sensors and magnetic sensors can also be present together in the sensor system of one or both devices.

Method

The method is divided into two substeps, for example: A) generation of the system, and B) recalibration of the system. Each of these substeps can contain one or more independent solutions.

A: Generation of the System:

In a first step, devices equipped effectively for measurement technology are made available in order to be able to fasten them to the body parts or to the dental arches of the lower jaw and to the dental arch of the upper jaw or alternatively to the upper jaw or the cranium. This gives submodules.

The submodules 20 for the upper jaw and 30 for the lower jaw are then produced. These are preferably fastened to the dental arch with a fastening device, to the upper jaw by means of 620 and to the lower jaw by means of 630; alternatively, the sensor elements are fastened directly to the tooth, for example by means of adhesive.

The sensory subsystems for the upper jaw and lower jaw are then activated by electrical energy, and measurable and detectable signals are generated by the elements of the submodules.

Preferably, sensory elements are grouped into sensor groups 21, 81 in order to be able to determine the relative position and relative movement in preferably 6 coordinates. In addition, the movement of the head, synonymous with the movement of the upper jaw, is determined with the aid of the subsystem.

Up to this step, everything can be prepared in advance, and the subsystems 20 and 30 can then be mounted on the rows of teeth.

B: Recalibration of the System

Movements are now carried out, and the movement of the upper jaw is detected directly, and the movement of the lower jaw is also detected directly and/or indirectly via its relative movement to the upper jaw.

If integral sensors are used, the measurement data are filtered and integrated, and in this way a trajectory is calculated in preferably six coordinates.

With the aid of the sensor group that is configured for the near distance, the coordinates of the lower jaw are now detected relatively as soon as the lower jaw lies in the exact measurement range of the sensor group for the near distance.

Either automatically or as soon as a signal for the recalibration is present, especially when the lower jaw approaches the upper jaw with approximation of the teeth, the measurement by the sensor group for the near distance is used in order in particular to also recalibrate the sensors for the far distance.

Subsequently or almost at the same time, the measurement values generated or supplied by the sensor group for the far distance before the recalibration are optionally corrected, in order in particular to achieve a correct harmonic transition in location, speed and acceleration.

When defined states of proximity are reached, for example the contact bite which forces a reversal of movement because no further approximation is possible, the sensors for the near distance are also calibrated if necessary.

When comparatively slow movement phases are reached, the sensor group for the far distance is optionally recalibrated if necessary.

Recalibration is made possible by generating the system with formation of a sensor group for the near distance and a sensor group for the far distance.

The recalibration is triggered by the movement into the near-distance range and further by the approximation and contact between the dental arches, in occlusion, and integration errors in the detection of the far distance and in the spatial six-dimensional movement of the bodies are thus compensated.

Further Exemplary Embodiments or Additions

In the proposed concept, upper jaw and lower jaw are preferably each detected with an at least 6 degrees-of-freedom sensor, i.e. possibly also with a 9 degrees-of-freedom sensor, which preferably also evaluates or can evaluate the force of gravity and the magnetic field, as in a navigation system. The measuring system in the mouth can be coupled directly to or on the teeth or implants by adhesive bonding or screwing or by similar means with a fixing effect. Or the measuring system is embedded in a splint or in some other connectable device, e.g. into a sleep-medicine protrusion splint or an orthodontic device.

In a particularly preferred embodiment, the system 100 comprises a magnetic field sensor in the sensor group 21 and/or 81. This detects a magnetic field that penetrates the body part in or on which the magnetic field sensor is applied. In the upper jaw 220, the magnetic field sensor preferably detects either the earth's magnetic field or a magnetic field that is built up in the surrounding space, in particular in order to be able to use a magnetic field that is stronger and by comparison easier to detect. In the lower jaw 230, the magnetic field sensor preferably detects a magnetic field which particularly preferably has an at least five times higher gradient and an at least five times higher strength than the earth's magnetic field and which is stationary relative to the upper jaw. With a suitable three-dimensional design of the magnetic field, the known geometry of the magnetic field of the magnetic element permits the position determination or movement detection or navigation of the lower jaw 230 relative to the upper jaw 220. For this purpose, the magnetic field generation can alternatively be attached not in the upper jaw 220 but in the lower jaw 230 and thus fixed with respect to the lower jaw 230 and, as a counterpart, the magnetic field sensors can be mounted in the upper jaw 220.

In a preferred embodiment of the system 100, the sensor groups 21 for the detection of the near distance and 81 for the detection of the far distance are composed of different metrologically effective elements and sensor types. The sensor group for the near distance comprises at least one magnetic-field-generating arrangement made of permanent magnetic material and at least one magnetic field sensor, the range of the defined magnetic field being limited to a few millimeters. By contrast, the sensor group for the far distance comprises a combination selected from rotation rate sensors and acceleration sensors, the signals of which are integrated.

In another preferred embodiment, the sensor group for the near distance comprises optical patterns or signal elements and also optical sensors. This optical sensor system works particularly preferably with the detection of patterns and interference patterns that arise at defined distances, in order to derive calibration signals from same.

In a further development, the sensor group for the near distance comprises a short-range magnetic-field-generating arrangement with permanent magnets, and the sensor group for the far distance comprises a long-range magnetic-field-generating arrangement with permanent magnets. In the near distance range, the measurement of the relative movement is supported or performed alone by the short-range magnetic-field-generating arrangement with permanent magnets, and in the far distance range by the long-range magnetic-field-generating arrangement in interaction with the respective magnetic field sensors on the opposite side. The permanent magnetic arrangements can be attached either to the side of the lower jaw or to the side of the upper jaw. The magnetic field sensors are attached to the opposite side and particularly preferably on the upper jaw side, because no signal supply is then required for the lower jaw.

In a further preferred embodiment, the relative movement of the upper jaw and thus of the skull in space is carried out via inertial sensors, this being recalibrated with the aid of a second sensor group, since otherwise, as has already been described, integration errors would arise because very slow and very rapid movements are in most cases not correctly detected and integrated. The recalibration takes place here not by means of a magnetic field sensor but by means of a gravity sensor, as soon as suitable rest phases or movement phases arise in which the gravity measurement can be carried out. A correction of the movement detection is then particularly preferably carried out in order to obtain harmoniously connected measurement curves for movement, speed and/or acceleration.

A preferred embodiment comprises an energy supply device and information transfer device. For this purpose, the proposed device 630 or also 620 preferably comprises a sensor device 631, a processor device 632, an energy storage device 633, an energy and data channel 634, and optionally an energy supply device 635, which is connected to the energy storage device 633. The components are coupled, preferably adhesively bonded or embedded in a fastening device, which can be fastened to the dental arch of the patient or test person with an individually tailored force-fit and form-fit engagement, preferably in a reversibly detachable manner, e.g. as a fixed brace or splint.

Finally, using the example of a two-part training device (see FIG. 7) which consists of modules 628 and 638, it is again shown how, in this particular embodiment, the coupling to the body parts lower jaw 230 and upper jaw 220 is effected and how the movement measurement is then carried out over a short or also a long period of time. The training device is, for example, used three times a day for twenty minutes, and the jaw movements should be recorded.

The devices 628, 638 are produced on the basis of individual scan data from dental arches and/or individual three-dimensional X-ray images and/or individual impressions, such that the depressions 226, 236 fit exactly to the dental arch and ensure an individually comfortable but also firm coupling between device and dental arch and thus jaws.

The devices for upper jaw and lower jaw are given a functionally suitable design in the mutually facing sides 670 and 680, in the exemplary embodiment a planar sliding surface.

The devices are given the functional elements 621, 622, 623, 624, 625, 626 integrated in the upper jaw part 620 ff and the functional elements 631, 632, 633, 634, 635, 636 and if necessary also 628, 638 or others in the lower jaw part 630 ff, and other elements.

The energy storage device is preferably charged before use.

The data connection is preferably established, unless the data logger is operating on memory.

The devices are inserted so that they are anchored with form-fit and force-fit engagement relative to the upper jaw or the lower jaw.

The movements are performed with the head and upper jaw and, relative thereto, also with the lower jaw.

The measurements meanwhile proceed and separately record the movements of the upper jaw and thus of the head and the movements of the lower jaw.

The positions are preferably determined by single or double integration of the sensor signals, if acceleration sensors or rotation rate sensors are involved.

Whenever the relative position comes into a calibration range of the calibration devices 626, 636, the coordinates of the devices 620ff, 630ff are recalibrated.

The movement curves are continued with the recalibrated values.

The values before the recalibration are optionally corrected if necessary.

The recalibration is repeated as often as possible as soon as the calibration devices 626, 636 come into the calibration range in which the calibration sensors can determine exact relative positions.

The recalibration with the position measurements has the great advantage that it is no longer necessary to provide integration in order to obtain the coordinates of the devices 620 ff and 630 ff; a very precise coordinate transformation is now sufficient. The calibration range in which the calibration devices can determine the relative position can be a defined relative position between upper jaw and lower jaw. This defined relative position can be a position that is often assumed in the usual sequence of movements, for example the occlusion position, or a position of upper and lower jaw relative to each other that the user of the system finds particularly comfortable. The defined relative position can therefore be user-specific. If the defined relative position is assumed, the new calibration or recalibration can take place, preferably automatically.

The respective sensor and/or the respective calibration device can be arranged intraorally. The entire respective device can be arranged intraorally, such that the respective jaw movement, for example during sleep, is not impeded by elements protruding from the mouth. This can significantly increase the acceptance of the proposed system by the users.

FURTHER DETAILS CONCERNING THE FIGURES

FIG. 1 shows a schematically represented skull with rows of teeth. The proposed system is used to detect the movements of the temporomandibular joint, with the lower jaw moving relative to the upper jaw, because the muscles attach to the cranium above and to the lower jaw below. In addition, however, there are superimposed movements of the cranium through the neck and through the neck muscles, and also the movements of the body itself. Therefore, the relative movement between lower jaw 230 and upper jaw 220 must be considered in order to be able to measure the relative movement of the teeth and the six-dimensional movements in the temporomandibular joint.

FIG. 2 shows the dental arches in what looks like a complete example, but with the wisdom teeth missing. The shape and size of the teeth and of the occlusal surfaces are highly individual. They are recorded digitally by three-dimensional imaging or by taking impressions, and this form of the dental arches is used to produce precisely fitting fastening elements and devices 620, 630.

FIG. 3*a* shows the device 630 inserted on the mandibular dental arch 231; the upper jaw 220 here does not have a device 620. This situation can be used in the system when the movement of the upper jaw is detected in another way, e.g. by coupling to the skull, especially in the case of an edentulous upper jaw prior to total reconstruction. From the point of view of the proposed system, it is therefore equivalent if the 6-degree-of-freedom coordinates of the movement of the upper jaw are obtained indirectly from the movement tracking of the head, as long as the coordinates are sufficiently precise as a function of time. FIG. 3*b* shows, as an exemplary embodiment, a subsystem for the lower jaw with an integrating sensor element 631 and further components 632 and an energy source 633 and a line connection 634 and a transmission device 635. Everything is integrated in the fastening element 630, which in this exemplary embodiment has the form of a standard aligner. The geometrical form of the for example splint-shaped devices 620 and 630 can be adapted to the individual dental arches and comprise rounded fissures and occlusal surfaces, as is shown in FIG. 5*a*. In this way, for example, the movement behavior when wearing an occlusal splint is simulated and made measurable. The components 632, 622 preferably contain processor devices that are supplied with energy via an energy source or an energy store. A memory for storing and keeping data ready is optionally integrated in the component 632. In addition, further sensor elements can be integrated. The data is optionally output via a radio signal or by other methods. Particularly preferably, the energy source 635, 625 is used with its antenna function in order to transmit the determined movement information to a receiver. The receiver can be an external computing device, e.g. a server or one of the processor devices located in the system. The antenna function of the energy supply element 635, 625 can therefore take over the transmission function and also the reception function for energy and also for data.

FIG. 4 shows different relative positions of the lower jaw with the same instrumentation. As soon as the patient or test person opens the jaw, rotations around up to three axes are superimposed with displacements in up to three spatial directions. The 6-degrees-of-freedom coordinates of the lower jaw change and mostly also those of the upper jaw, but in particular the relative position of the lower jaw to the upper jaw, which results from the two sets of coordinates of upper jaw and lower jaw. In the proposed concept, the upper jaw sensor 621 with processor unit 622 generates an upper jaw coordinate system with the axes 651, 652, 653, and the lower jaw sensor 631 with processor unit 632 generates a coordinate system 661, 662, 663, which is different in space in the origin of the position (coordinate system) and in which the axes have different spatial orientations. Comparison between FIG. 4*a* and FIG. 4*b* reveals the difference whereby at the bottom in FIG. 4*a* the lower jaw 230 is pushed significantly further forward in the direction of the axis 662, such that there is a protrusion position in FIG. 4*b*.

FIG. 5*a* shows the instrumented rows of teeth from FIG. 4 in a closed position, in the contact bite, wherein the fastening devices here act as an occlusion splint and create an additional distance between lower jaw and upper jaw. If, on the other hand, fastenings are used that do not cover the occlusal surface but only hold laterally, the dental arches can come closer together.

FIG. 5*b* shows a device 600 which is used for biomechanical training and which consists of the modules 628 and 638. The training function is provided here by the planar sliding surface 640 at which upper jaw part 628 and lower jaw part 638 can slide into contact. In the case of contact with moist surfaces, the friction is very low and, consequently, the musculature has to stabilize the position due to the lack of occlusal retention. This leads to special and neurophysiologically very useful training effects, which can now be recorded by the processor devices 632 and 622 with the aid of the movement detection in the sensors 631 and 621.

FIG. 6 shows two different fastening variants that do not provide occlusal cover. For particularly long-term applications, the functional elements, as shown schematically in FIG. 6*a* with e.g. sensor unit 631, 621, processor and storage unit 632, 622, energy storage 633, 623 etc., can each be fastened directly or in the manner of bonded bracket fixations to the teeth or also to implants, such that it is not necessary to use a splint with individually shaped regions for the dental arches in order to achieve the same result. This has the advantage that there is no relative movement between fastening rail and dental arch, although the tooth which carries the movement sensor can move differently than the jaw, because the tooth is elastically suspended in the jaw.

FIG. 6*b* shows so-called non-occlusal attachments as laterally holding braces that leave the occlusal surfaces free and thus permit the natural contact of the dental arches. These are used to measure and dynamically observe the unimpeded occlusion that the proposed assemblies provide laterally on the lingual or tongue side and/or the buccal or cheek side or the labial or lip side, wherein the occlusal surfaces are not covered but instead remain free. Such devices 627, 637 are mostly in the form of a brace and are often individually adapted and held in place by clamping forces and/or by adhesive.

FIG. 7*a* shows a proposed embodiment for improving accuracy. In this case, a plurality of sensor elements 621, 681 and 631, 691 per dental arch or per body part are used or applied and coupled within a subsystem for the upper jaw or lower jaw. This is done in a proposed concept in order to be able to detect different aspects of the movement in an optimized manner simultaneously with the two sensor elements. In a particularly preferred embodiment, one sensor element can very effectively track and integrate slow movements, while the other sensor element can very effectively detect rapid movements and high accelerations.

The two sensor types can also be integrated in a sensor module; they can, but do not have to be, attached to different locations of the device. In a particular embodiment, one of the sensor elements 681 is located further back in the molar region, if this is functionally advantageous, and another sensor element 621 is located further forward in the region of the canines or incisors. This arrangement can be used, for example, in order to detect the near region particularly effectively with one sensor element 621 and the far region, with wide opening of the jaw, with the other sensor element 681. The distance can be used here to achieve the appropriate range of movement or, for example, to better resolve spatial magnetic fields using sensors. The overdetermination of the measurement with two or more 6-degree-of-freedom sensors can also be used for error correction and also for the determination of elastic or permanent plastic distortions in the device 620 ff and 630 ff.

FIG. 7b shows a further important use of movement detection, in particular for measuring the nocturnal jaw movement when snoring with and without an anti-snoring splint. Shown schematically is an at least two-part anti-snoring splint with upper jaw module 628 and lower jaw module 238. As an anti-snoring splint, protrusion splints are preferably used which push the lower jaw forward with the force F, the forward pushing force being effected through mechanical elements such as rods or levers or hooks or inclined toothing elements 938, 928. The proposed integrated sensor system uses the modules 628 and 638 of the anti-snoring splint instead of the fastening elements 620 and 630. The combination of different sensor elements 621, 622 or 631, 632 permits the precise detection of the movement both in the near range with force contact and also in the far range with the mouth open. In particular, the proposed recalibration of the sensor system permits long-term accurate movement detection by means of integration errors etc. being repeatedly corrected. The recalibration of the relative detection of the lower jaw movement permits in particular the correction of slow detection errors that would otherwise arise over the course of a night. Moreover, for the movement of the head, the recalibration is carried out by comparison with an extended sensor system with gravity measurement, such that the otherwise very disruptive integration errors are also corrected here.

FIG. 8 shows a possible definition of the mutually perpendicular main spatial axes for the systems of the upper jaw and the lower jaw. The vertical main axes 661 of the lower jaw and 651 of the upper jaw remain parallel only in the case of pure translation. However, the temporomandibular joint generally permits free complex movements in which the main axes of the lower jaw can be shifted in three spatial directions in relation to the upper jaw and can also be rotated around three mutually perpendicular rotation axes. Together there are generally six degrees of freedom of movement, as long as the movement is not restricted as in the case shown here. In FIG. 8c, the lower jaw is shifted parallel to the right, such that it appears shifted to the left in the image from the front. In the event that integrating sensors are used, very precise filtering and integration is necessary in order to be able to detect such small displacements precisely enough. Dental biomechanics and movement analysis require accuracies of around ten to fifty micrometers as soon as the design of corresponding occlusal surfaces is concerned. Devices as shown here can be used on the one hand to test, so to speak, the directional separation of the measuring system. In addition, they have a very impressive therapeutic effect.

FIG. 9 shows the generation of sensor pairs 621 and 631 or 681 and 682 at the top and bottom, in order to be able to detect the relative position even more precisely with this pairing. The sensor pair uses an interaction 22, 82 between the sensor elements in order to infer therefrom the relative position. FIG. 9a shows the mouth open, FIG. 9b shows it in a closed position. A sensor pair consists, for example, of a permanent magnet arrangement (as sensor exciter) and a magnetic field sensor which detects and evaluates the spatially structured magnetic field of the permanent magnet arrangement in order thereby to infer a relative coordinate relationship between upper jaw and lower jaw. The sensor pairs in the system can have different accuracy ranges and are used in accordance with the optimized accuracy in order to compensate for weaknesses of the other sensor pairs. Thus, within the context of the proposed solution, it is possible to detect the complex movements precisely and with the highest possible resolution.

FIG. 10 shows an exemplary embodiment with two sensor pairs, wherein two different sensors 621, 681 and 631, 691 are integrated in a component 622, 632. FIG. 10a shows the mouth opened, while FIG. 10b shows it in a closed position. One sensor pair can, for example, detect a magnetic interaction and provide it for evaluation, and another pair can, for example, detect a gravitational interaction. In such a combination, an inertial sensor can also be integrated which detects and integrates accelerations and/or rotation rates. The optimum effect of the magnetic sensor pairs is often in the close range, while the gravimetric sensor pairs or sensors determine where down is, e.g. in order to keep detecting the direction from the bottom upward during sleep, despite the head movement. The short-range magnetic field sensors can be better used to precisely measure the near distance when the lower jaw approaches the upper jaw or during transitioning to the contact bite and, if necessary, to trigger a recalibration, in particular of an inertial sensor.

FIG. 11 shows a particular exemplary embodiment with an extension 623 or 633 of the fastening elements 620 or 630 that protrudes outward from the mouth. As a result, the sensor elements come into the region outside the mouth and the lips. This is necessary, for example, when introducing the components would trigger allergies or disturbances or if the sensors would be disturbed by implants. With the extended fastening devices leading outward, the extents of movement are increased in the sense of the lever principle. The coordinate transformations in the movement detection take these relationships into account. However, this only leads to improved accuracy if the fastenings are stiff enough. Outward extensions of the fastening elements can mainly be used for a short period of time. They have the advantage of offering more space for the energy supply and better information transfer.

FIG. 12 shows, purely schematically, the proposed system 100 with the subsystems 20 for the upper jaw and 30 for the lower jaw only with the fastening devices 620 or 630 and without the dental arches, in order to achieve better clarity. The sensor pairs 21 and 81 shown in broken lines each connect a sensor element from the subsystem of the upper jaw to a sensor element from the subsystem of the lower jaw and evaluate an interaction. Possible sensor systems work optically with detection of graphic patterns or magnetically with detection of permanent magnetic fields or gravimetrically with detection of the direction of gravity. Ultrasound systems are also possible in which one side sends out impulses and the other receives them shortly thereafter. In the context of the proposed solution, at least one sensor pair is evaluated in order to detect the relative movement and relative position of upper jaw and lower jaw. Two different or differently configured sensor pairs are particularly preferably detected, and the signals are evaluated in order to achieve, from the combination of the signals, a further improved resolution and/or accuracy. One of the sensor pairs is particularly preferably used to trigger a recalibration of sensors, in particular of the integrating sensors.

The components of the system can be provided for intraoral use or extraoral use. Mixed forms are also possible, such as the Aspects Several sets of aspects of the disclosure are set forth below, with the aspects being numbered in order to facilitate the reference of the features of one aspect in other aspects. These aspects or sets are to be regarded as an independent disclosure which, if necessary, can be made the subject of patent claims. The aspects are also to be viewed as a disclosure supplementing the further disclosure, such that features that are described in the aspects can also be used in a context other than the context described, in particular in combination with features from the remaining parts of the description. Furthermore, the features of individual aspects can also be viewed in isolation, i.e. without reference to higher-ranking aspects.

1. System (100) for movement detection with or composed of at least two devices (620, 630) for preferably form-fit and/or force-fit coupling to body parts, in particular to the upper jaw (220) or lower jaw (230), each with sensor combinations or inertial sensors and electronics (621, 622) or (631, 632) which, for example independently or predominantly independently, measure the for example complex movement of upper jaw (220) and lower jaw (230) or are designed for the associated measurement, and electronics, in particular a processor device, which can determine therefrom the relative movement between upper jaw and lower jaw, the relative movement in the temporo-mandibular joint and/or the head movement, or is designed to determine in particular the respective movement or relative movement.

2. System for movement detection, in particular on the dentition and on the temporomandibular joint, according to one of the preceding aspects, wherein at least one of the subsystems (20, 30), in particular for upper jaw or lower jaw, has at least one calibration sensor (626, 636), wherein the calibration sensor in one locally delimited range of the movement possibilities, in particular in the range of the occlusal approximation of upper jaw and lower jaw, determines the instant relative position of the two devices (620, 630) or, in a longer relative rest phase, determines the six-dimensional spatial position and spatial orientation of the upper jaw device (620) and thus permits recalibration of parts of the system (100) and a correction of previous and future measurements.

3. System for movement detection according to one of the preceding aspects, wherein at least one of the subsystems (20, 30) comprises at least two different or differently configured sensor elements, and the sensor elements are selected and configured such that one is configured more for the detection of the near distance and another is configured more for the detection of the far distance of the functionally decisive regions of the body parts, in particular of the dental arch of the lower jaw from the dental arch of the upper jaw.

4. System for movement detection according to one of the preceding aspects, wherein at least one sensor of the subsystem (20) or of the subsystem (30) detects an interaction between the subsystems (20, 30), selected from magnetic field sensor, light sensor, ultrasonic sensor or gravitation sensor, and this signal is used to increase the measurement accuracy of other sensors or to trigger a recalibration or a correction in the system (100).

5. System for movement detection according to one of the preceding aspects, wherein at least one sensor pair composed of at least one element of the subsystem (20)

and at least one element of the subsystem (30) is used in order to detect a measurable and evaluable interaction between the elements (621, 622, 631, 632, 681, 691) of the subsystems (20, 30).

6. System for movement detection according to one of the preceding aspects, wherein at least one sensor pair (21, 81) is formed by at least one permanent magnet and at least one magnetic field sensor or at least one optically recognizable pattern and an optical sensor or at least one ultrasound source and an ultrasound receiver, and wherein further sensor signals, in particular inertial sensors or other types of sensors, are used to detect at least the six-dimensional position of one of the subsystems.

7. System (100) for movement detection according to one of the preceding aspects, wherein at least one gravitation sensor is used to determine the direction of gravity for at least one of the subsystems at least temporarily or repeatedly, in particular for the upper jaw subsystem (620), wherein other sensors are moreover used in order to detect the movement or the relative movement of the other subsystem, in particular of the lower jaw subsystem (630).

8. System, preferably according to one of the preceding aspects, comprising the components of a protrusion splint (627, 637) for anti-snoring therapy or for apnea therapy or a training device with transverse separating surfaces (670, 680).

9. System, preferably according to one of the preceding aspects, having at least two sensors of different sensitivity for at least one of the devices (620, 630) or per dental arch, wherein one of the two sensors is configured for predominantly rapid movements and the other for predominantly slow movements.

10. Method for detecting positions, movements and relative movements of body parts, in particular of upper jaw and lower jaw with the upper and lower dental arches, using the system according to one of the preceding aspects, by performing the following method elements:
   a) making available subsystems (20, 30) with fastening elements (620, 630) and integrated sensors and electronics (621, 622, 631, 632, 681, 691) and also elements for energy supply, data processing and information transfer and information storage,
   b) fastening the subsystems (20, 30) to the body parts, in particular to the dental arches (221, 231) of the upper jaw (620) and lower jaw (630),
   c) activating the energy supply of the sensor systems in the subsystems and the other elements,
   d) performing movements and relative movements of the body parts, in particular of the lower jaw relative to the upper jaw,
   e) capturing the data determined by sensors in the subsystems (20, 30),
   f) intermediate storage or transfer of the captured sensor data, in particular of the information on the movement of the lower jaw and/or the upper jaw,
   g) determining the movement data of at least one body part, in particular of at least the lower jaw or the upper jaw or the relative movement between lower jaw and upper jaw.

11. Method for detecting positions, movements and relative movements of body parts, in particular of upper jaw and lower jaw with the upper and lower dental arches, using the system according to one of the preceding aspects, by performing the following method elements:
a) detecting the sensory signals of at least one inertial sensor of the first subsystem (20) and of at least one inertial sensor of the second subsystem (30) and transferring this information to electronics or software in order to determine therefrom the data of the relative movement of the two body parts in up to 6 degrees of freedom of movement.

12. Method for detecting positions, movements and relative movements of body parts, in particular of upper jaw and lower jaw with the upper and lower dental arches, using the system according to one of the preceding aspects, by performing the following method elements:
a) detecting the sensory signals of at least one inertial sensor of the first subsystem (20) or of the second subsystem (30) and transferring this information to electronics or software in order to determine therefrom the data of the relative movement of the body part in up to 6 degrees of freedom of movement,
b) detecting the movement in the region of a calibration range of a third sensor or sensor pair and then triggering a calibration or correction of the sensor configuration of the inertial sensor.

13. Method for detecting positions, movements and relative movements of body parts, in particular of upper jaw and lower jaw with the upper and lower dental arches, using the system according to one of the preceding aspects, by performing the following method elements:
a) detecting the sensory signals of at least one first sensor of the subsystem (20) or of the second subsystem (30),
b) detecting the movement in the region of a calibration range of a third sensor or sensor pair and then triggering a calibration or correction of the sensor configuration of the first sensor,
c) carrying out a correction to the previously recorded and determined movement data, in particular in the sense of adjusting the previously recorded trajectories to the new calibration.

14. Method for detecting positions, movements and relative movements of body parts, in particular of upper jaw and lower jaw with the upper and lower dental arches, using the system according to one of the preceding aspects, by performing the following method elements:
a) detecting the movement in a region of the near distance by a first sensor pair configured for this purpose or a first sensor configured for this purpose,
b) detecting the movement in a region of the far distance by a second sensor pair configured for this purpose or a second sensor configured for this purpose,
c) using the sensor signal for the near range in order, when approaching a suitable calibration region within the near range, to trigger a calibration process or a correction process and to store or transmit calibration values or correction values.

15. Method for detecting positions, movements and relative movements of body parts, in particular of upper jaw and lower jaw with the upper and lower dental arches, using the system according to one of the preceding aspects, by performing the following method elements:

a) detecting the movement of at least one of the subsystems (20, 30) in space, in particular of the subsystems for upper jaw and/or lower jaw,
b) detecting the gravitational field or a sensor signal coupled to the gravitational field and to its direction,
c) detecting a calibration range within the movement sequence, in particular a range of uniform movement or approximated rest or of suitable spatial orientation of the gravimetric sensor,
d) triggering a calibration of the spatial orientation at least of the subsystem detected, in particular of the upper jaw subsystem.

A further set of aspects is set forth below.
1. System with or composed of at least two devices for preferably form-fit and/or force-fit coupling to the upper jaw or lower jaw, each with sensor combinations or inertial sensors (621, 631) which independently measure the complex movement of upper jaw and lower jaw, and a processor device (622, 632) which can determine therefrom the relative movement between upper jaw and lower jaw, the relative movement in the temporomandibular joint and/or the head movement or is designed to determine the respective (relative) movement.
2. System according to one of the preceding aspects, wherein the preferably respective device, in particular the one above (upper jaw) and/or below (lower jaw), has at least one calibration sensor (626, 636), wherein the in particular respective calibration sensor, for example in a local measuring region and/or in a temporary movement phase or also in a longer relative rest phase, determines the exact relative position of the two devices and thus permits a new calibration of the position, in particular of the relative position between upper jaw and lower jaw.
3. System with devices (620, 630), preferably according to one of the preceding aspects, wherein the interfaces between upper jaw and lower jaw are designed according to the desired function and differ from a normal occlusal splint or a normal aligner.
4. System, preferably according to one of the preceding aspects, comprising the components of a protrusion splint (627, 637).
5. System, preferably according to one of the preceding aspects, comprising the components (628, 638) of a training device with transverse separating surfaces (670, 680).
6. System, preferably according to one of the preceding aspects, with at least two sensors of different sensitivity for at least one of the devices (620, 630) or per dental arch, combined with adaptation of one sensor for rapid movements and of the other sensor for slow movements.
7. System or method for measuring movements and relative movements, preferably by means of a system according to one of the preceding aspects, wherein upper jaw and lower jaw devices (620, 630) with inertial sensors are used above and below, which permit a movement measurement and, on the basis thereof, a determination of relative positions by integration of accelerations or speeds.
8. System or method according to aspect 7, wherein the sensors determine the movements in at least three translation coordinates and three rotation coordinates, i.e. coordinate systems of the devices comprising 6 degrees of freedom, preferably by adding and/or integrating sensor signals from acceleration meters and/or rate of rotation meters.

9. System or method according to aspect 7 or 8, wherein, in the movement sequence, accidentally or intentionally, calibration ranges in the relative position are temporarily set as the body position, and an exact measurement of the relative position takes place in these movement ranges, preferably with the aid of the calibration devices (626, 636).

10. System or method according to aspect 7, 8, and/or 9, wherein subsequently, in particular after the measurement of the exact relative position, a correction of the trajectories and positions and orientations takes place corresponding to the new calibration.

LIST OF REFERENCE SIGNS

1-8 identification of the tooth positions in the dental arch, individually often incomplete
20 subsystem with sensors and electronics for the upper jaw
21 first sensor pair
22 interaction between sensor pair 21
30 subsystem with sensors and electronics for the lower jaw
81 second sensor pair
82 interaction between sensor pair 81
100 overall system
200 head or skull
220 upper jaw
221 dental arch of the upper jaw
222 applied occlusal plane of the upper jaw in an approximation as a flat surface
226 depressions for or impressions of the teeth of the upper jaw
230 lower jaw
231 dental arch of the lower jaw
232 applied occlusal plane of the lower jaw in an approximation as a flat surface
236 depressions for or impressions of the teeth of the lower jaw
240 mouth interior with the mouth opened
270 condyles of the temporomandibular joint
272 articular surface on the upper jaw
273 articular surface on the lower jaw
400 method
620 upper jaw device, e.g. splint-shaped, individually matching the dental arch 221
621 six-degrees-of-freedom-capable movement sensor in the upper jaw part
622 processor device with storage unit for data in the upper jaw
623 energy storage in the upper jaw
624 energy and data line in the upper jaw
625 energy and data antenna in the upper jaw
626 calibration device in the upper jaw
627 non-occlusal attachment, leaves occlusal surfaces of the upper jaw free
628 upper jaw training device, with sliding surface 640
630 lower jaw device, e.g. splint-shaped, individually matching the dental arch 221
631 six-degrees-of-freedom-capable movement sensor in the lower jaw part
632 processor device with storage unit for data in the lower jaw
633 energy storage in the lower jaw

634 energy and data line in the lower jaw
635 energy and data antenna in the lower jaw
636 calibration device in the lower jaw
637 non-occlusal attachment, leaves occlusal surfaces of the lower jaw free
638 lower jaw training device, with sliding surface 640
651 coordinate axis of the upper jaw system upward
652 coordinate axis of the upper jaw system forward
653 coordinate axis of the upper jaw system to the right
661 coordinate axis of the lower jaw system upward
662 coordinate axis of the lower jaw system forward
663 coordinate axis of the lower jaw system to the right
670 sliding surface on the upper jaw part 628
680 sliding surface on the lower jaw part 638
701 coordinate axis upward to the crown
702 coordinate axis forward to the mouth opening
703 coordinate axis to the right toward the right cheek in relation to the head
711 rotation axis vertical top to bottom parallel to 701
712 rotation axis from rear to front lying parallel to 702
711 rotation axis from left to right running parallel to 703
928 mechanical element for generating a force on the upper jaw
929 constraining force F on the upper jaw
938 mechanical element for generating a force on the lower jaw
939 constraining force on the lower jaw

Glossary

6DOF: 6 Degrees of Freedom 6 degrees of freedom: Six mechanical degrees of freedom of movement, a position definition or translation in three spatial directions and superimposed a rotation about three spatial angles around the main axes Accelerometer: Acceleration meter which does not speed or position but acceleration forces and consequently must be integrated twice on this basis in order to obtain the position Movement measurement: Sequence of recordings over a period of time in which movements of the detected objects or body parts and devices take place Buccal: Toward the cheek Fastening element: Mechanically coded form-fit and force-fit element for coupling a coupling element to an object, a holder or a body part, with at least one mechanical interface for the mechanically reversibly releasably fixed coupling of a coupling element Rate of rotation sensor: Sensor which measures the speed of rotation, mostly utilizing the forces caused by rotation, to determine the angular position, and so has to be integrated once via the rate of rotation Body part: Object whose movement is to be measured, e.g. lower jaw or skull with upper jaw Coupling element: Mechanically code form-fit and force-fit connection element for the reversibly releasable and restorable coupling of a measurement system or of a marker body to the fastening elements Labial: Toward the lips Lingual: Toward the tongue Non-occlusal: Not covering the occlusal surfaces, so that it is possible to bite down unimpeded Processor unit: Data technology device which comprises computer elements, data memory, software memory, main memory, data channels and energy supply elements and usually also cooling elements Right: In relation to the head, toward the right cheek, and therefore, as seen in the image from the front, toward the left Six-dimensional: Generally comprising three dimensions of translation and three dimensions of rotation, corresponding to six physical degrees of freedom of movement Interaction: Physically or electronically evaluable interaction between a cause and a sensor or a transmitter and a receiver, where optionally both sides can transmit and receive, e.g. magnetic field generator and magnetic field sensor Point in time: Preferably short measuring and recording interval for which the measurement value is determined, finite duration, i.e. somewhat fuzzy

The invention claimed is:

1. A system for detecting relative movement of body parts, the system having at least a first subsystem and a second subsystem, wherein the first subsystem is designed to be fastened to a first body part, the first body part being an upper jaw, or a body region rigidly connected to the upper jaw, and the second subsystem is designed to be fastened to a second body part, the second body part being a lower jaw, wherein the first body part and the second body part are movable relative to each other, and wherein the system comprises a movement sensor system and a calibration sensor system, wherein the movement sensor system is designed to detect the relative movement or a relative position of the first body part and the second body part across a movement region, by generating data from which a movement trajectory or course of the relative movement of the first body part and of the second body part can be obtained or is obtained, and the calibration sensor system is designed to determine the relative position of the first body part relative to the second body part if the first body part and the second body part are arranged relative to each other in a calibration region, wherein the system is designed to compare a current relative position, obtained by means of the calibration sensor system, with a relative position obtained at a same time by means of the movement sensor system, in order to carry out a calibration alignment, and wherein if the calibration alignment shows that the compared relative positions are different, the system is designed to transfer the current relative position, determined by means of the calibration sensor system, to the movement sensor system, such that the movement sensor system can use the current relative position as a starting point for a further movement detection.

2. The system of claim 1, wherein the calibration sensor system and/or the movement sensor system is designed to determine the relative positions in 6 degrees of freedom (six coordinates: three in rotation, three in translation).

3. The system of claim 1, wherein only if the calibration alignment shows that the compared relative positions are different, the system is designed to transfer the current relative position, determined by means of the calibration sensor system, to the movement sensor system, such that the movement sensor system can use the current relative position as the starting point for the further movement detection.

4. The system of claim 1, wherein only if the calibration alignment shows that the compared relative positions are different, the system is designed, on a basis of the current relative position, to modify the trajectory determined by means of the movement sensor system before the calibration alignment, such that the trajectory leads through the current relative position.

5. The system of claim 1, wherein the system is designed such that a modification comprises a smoothing of the trajectory.

6. The system of claim 1, wherein the system is designed such that a modification adapts the trajectory to a natural movement.

7. The system of claim 1, wherein the calibration sensor system and/or the movement sensor system is designed to determine the movement trajectory or course in 6 degrees of freedom (six coordinates: three in rotation, three in translation).

8. The system of claim 1, wherein the system is designed to use data, obtained by means of the calibration sensor system, for checking data obtained by means of the movement sensor system.

9. The system of claim 1, wherein the movement region comprises all of the relative positions that can be assumed by the first and the second body part relative to each other.

10. The system of claim 1, wherein the calibration region is a true subset of the movement region.

11. The system of claim 1, wherein the calibration region comprises an occlusion position between the upper jaw and the lower jaw and/or comprises a region adjacent to the occlusion position.

12. The system of claim 1, wherein the calibration region is less than or equal to one of the following percentages of the movement region: 30%, 25%, 20%, 15%.

13. The system of claim 1, wherein the calibration sensor system has, in the calibration region, a measurement accuracy which is greater than a measurement accuracy of the movement sensor system.

14. The system of claim 1, wherein the calibration sensor system has, in the calibration region, a resolution which is at least 2 times as high as an average resolution of the movement sensor system in the movement region.

15. The system of claim 1, wherein the first subsystem has a subsystem carrier which is designed for fastening to the first body part.

16. The system of claim 1, wherein the second subsystem has a second subsystem carrier which is designed for fastening to the second body part.

17. The system of claim 1, wherein a first system carrier and/or a second system carrier is designed to function as a carrier for at least one component of the calibration sensor system and/or of the movement sensor system.

18. The system of claim 1, wherein the calibration sensor system has at least one calibration sensor.

19. The system of claim 18, wherein the calibration sensor is a magnetic field sensor.

20. The system of claim 18, wherein the calibration sensor system has at least one calibration sensor exciter which is designed to generate a sensor signal in the calibration sensor.

21. The system of claim 20,
wherein the calibration sensor exciter is a magnet.

22. The system of claim 20,
wherein the calibration sensor is part of the first subsystem and the calibration sensor exciter is part of the second subsystem, or
wherein the calibration sensor is part of the second subsystem and the calibration sensor exciter is part of the first subsystem.

23. The system of claim 18,
wherein the calibration sensor system is free of a sensor exciter.

24. The system of claim 18,
wherein the calibration sensor is part of the first subsystem or of the second subsystem.

25. The system of claim 1,
wherein the movement sensor system comprises at least one movement sensor.

26. The system of claim 25,
wherein the movement sensor is an inertial sensor or an optical sensor.

27. The system of claim 25,
wherein the movement sensor system has at least one movement sensor exciter which is designed to generate a sensor signal in the movement sensor.

28. The system of claim 27,
wherein the movement sensor exciter is one of the following exciters:
    a radiation source or a radiation source matched to an optical sensor.

29. The system of claim 27,
wherein the movement sensor is part of the first subsystem and the movement sensor exciter is part of the second subsystem, or
wherein the movement sensor is part of the second subsystem and the movement sensor exciter is part of the first subsystem.

30. The system of claim 25,
wherein the movement sensor system is free of a sensor exciter.

31. The system of claim 25,
wherein the movement sensor is part of the first subsystem or of the second subsystem.

32. The system of claim 1,
wherein a calibration sensor and a movement sensor are part of different subsystems.

33. The system of claim 1,
wherein a calibration sensor and a movement sensor are part of the same subsystem and are fastened to a common subsystem carrier.

34. The system of claim 1,
comprising a plurality of calibration sensors, of which a first calibration sensor is part of the first subsystem and a second calibration sensor is part of the second subsystem.

35. The system of claim 1,
comprising a plurality of movement sensors, of which a first movement sensor is part of the first subsystem and a second movement sensor is part of the second subsystem.

36. The system of claim 1,
wherein a movement sensor and/or a calibration sensor is an integral sensor.

37. The system of claim 1,
wherein a calibration sensor and/or a movement sensor is a contactless sensor.

38. The system of claim 1,
wherein a calibration sensor and/or a movement sensor is a contact sensor.

39. The system of claim 1, wherein the system comprises a spatial position sensor system which is designed to determine an absolute position of the first body part or of the second body part in 6 degrees of freedom.

40. The system of claim 1,
wherein a spatial position sensor system is a sensor system without a sensor exciter.

41. The system of claim 1,
wherein a spatial position sensor system has a spatial position sensor.

42. The system of claim 1,
wherein the system comprises an orientation sensor system which is designed to determine an orientation of the first body part or of the second body part in space.

43. The system of claim 1,
wherein an orientation sensor system comprises an orientation sensor.

44. The system of claim 1,
wherein the system comprises a processor device, which is designed:
    to control the movement sensor system and/or the calibration sensor system, and/or
    to carry out the comparison of the relative positions.

45. The system of claim 1,
wherein the system has an electrical power source.

46. The system of claim 1,
wherein the system has a storage device, in particular a data memory.

47. The system of claim 46,
wherein the storage device is designed for intermediate storage of data of the movement sensor system.

48. The system of claim 46,
wherein the system is designed such that it deletes data stored in the storage device after the calibration alignment, after correction or alignment of the data of the movement sensor system to the current relative position, and/or before a next calibration alignment.

49. The system of claim 1,
wherein any component, any selected plurality of components or all of the following components of the system are designed to be arranged intraorally when the system is in operation:
    movement sensor(s),
    calibration sensor(s),
    spatial position sensor,
    gravity sensor,
    processor device,
    electrical power source,
    storage device.

50. The system of claim 1,
wherein any component, any selected plurality of components or all of the following components of the system are designed to be arranged extraorally when the system is in operation:
    movement sensor(s),
    calibration sensor(s),
    spatial position sensor,
    gravity sensor,
    processor device,
    electrical power source,
    storage device.

* * * * *